(12) United States Patent
Dorsch et al.

(10) Patent No.: US 8,815,924 B2
(45) Date of Patent: Aug. 26, 2014

(54) HETEROCYCLIC CARBONYL COMPOUNDS

(75) Inventors: Dieter Dorsch, Ober-Ramstadt (DE); Rolf Gericke, Seeheim-Jugenheim (DE); Werner Mederski, Zwingenberg (DE); Norbert Beier, Reinheim (DE); Florian Lang, Tuebingen (DE)

(73) Assignee: Merck Patent GmbH, Darmstadt (DE)

( * ) Notice: Subject to any disclaimer, the term of this patent is extended or adjusted under 35 U.S.C. 154(b) by 1055 days.

(21) Appl. No.: 11/665,854

(22) PCT Filed: Apr. 4, 2005

(86) PCT No.: PCT/EP2005/003514
§ 371 (c)(1),
(2), (4) Date: Apr. 20, 2007

(87) PCT Pub. No.: WO2006/045350
PCT Pub. Date: May 4, 2006

(65) Prior Publication Data
US 2008/0090882 A1 Apr. 17, 2008

(30) Foreign Application Priority Data
Oct. 21, 2008 (DE) .......... 10 2004 051 277

(51) Int. Cl.
| | |
|---|---|
| *A61K 31/421* | (2006.01) |
| *A61K 31/422* | (2006.01) |
| *A61K 31/416* | (2006.01) |
| *A61K 31/4178* | (2006.01) |
| *A61K 31/341* | (2006.01) |
| *C07D 413/00* | (2006.01) |
| *C07D 413/02* | (2006.01) |
| *C07D 233/54* | (2006.01) |
| *C07D 231/56* | (2006.01) |
| *C07D 307/34* | (2006.01) |

(52) U.S. Cl.
CPC ............ *A61K 31/421* (2013.01); *A61K 31/422* (2013.01); *A61K 31/416* (2013.01); *A61K 31/4178* (2013.01); *A61K 31/341* (2013.01); *C07D 413/00* (2013.01); *C07D 413/02* (2013.01); *C07D 233/54* (2013.01); *C07D 231/56* (2013.01); *C07D 307/34* (2013.01)
USPC ........... 514/374; 514/397; 514/400; 514/403; 514/461; 549/487; 548/236; 548/311.7; 548/362.5

(58) Field of Classification Search
CPC . A61K 31/421; A61K 31/422; A61K 31/416; A61K 31/4178; A61K 31/341; C07D 413/00; C07D 413/02; C07D 233/54; C07D 231/56; C07D 307/34
USPC .................. 514/397, 400, 403, 461; 548/236, 548/311.7, 362.5; 549/487
See application file for complete search history.

(56) References Cited

U.S. PATENT DOCUMENTS

| | | | |
|---|---|---|---|
| 3,455,837 A | 7/1969 | Maeder et al. | |
| 3,852,293 A | 12/1974 | Ariyan et al. | |
| 4,879,295 A * | 11/1989 | Yoshinaga et al. | ....... 514/255.05 |
| 5,284,821 A | 2/1994 | Ditrich et al. | |
| 5,374,605 A | 12/1994 | Hallenbach et al. | |
| 5,591,695 A | 1/1997 | Newton et al. | |
| 5,591,776 A | 1/1997 | Cavalla et al. | |
| 5,886,191 A * | 3/1999 | Dominguez et al. | .......... 548/491 |
| 6,555,501 B1 * | 4/2003 | Bastiaans et al. | ............ 504/252 |
| 7,313,157 B2 | 12/2007 | Sorin et al. | |
| 2003/0139404 A1 | 7/2003 | Haag et al. | |
| 2004/0214888 A1 * | 10/2004 | Matsuura et al. | ............. 514/522 |

FOREIGN PATENT DOCUMENTS

| | | |
|---|---|---|
| CA | 1 055 036 | 5/1979 |
| CA | 2 516 118 | 8/2004 |
| EP | 0 419 944 A | 4/1991 |
| EP | 647635 | 4/1995 |
| EP | 0 726 263 A2 | 8/1996 |
| GB | 1 390 402 | 4/1975 |
| GB | 1 390 402 A | 4/1975 |
| GB | 1 492 663 A | 11/1977 |
| JP | 48 092369 | 11/1973 |
| JP | 49 007052 | 2/1974 |
| JP | 49 049969 | 5/1974 |
| JP | 51 125379 | 11/1976 |
| JP | 03 145478 | 6/1991 |
| JP | 05 279351 | 10/1993 |
| JP | 08 027130 | 1/1996 |
| JP | 1996-27130 | 1/1996 |
| JP | 08 311064 | 11/1996 |
| JP | 10 502354 | 3/1998 |
| JP | 2007 515792 | 6/2007 |
| WO | WO 96/00218 A | 1/1996 |
| WO | WO 96/16040 | 5/1996 |

(Continued)

OTHER PUBLICATIONS

Morissette et al. Advanced Drug Delivery Reviews 2004, 56, 275-300.*

(Continued)

*Primary Examiner* — Samantha Shterengarts

(74) *Attorney, Agent, or Firm* — Millen, White, Zelano & Branigan, P.C.

(57) ABSTRACT

Novel heterocyclic compounds of the formula (I), in which $R^1$, D, W, T and T' have the meanings indicated in Claim 1, are SGK inhibitors and can be used for the treatment of SGK-induced diseases and conditions, such as diabetes, obesity, metabolic syndrome (dyslipidaemia), systemic and pulmonary hypertonia, cardiovascular diseases and kidney diseases, generally in fibroses and inflammatory processes of any type.

46 Claims, No Drawings

(56) References Cited

FOREIGN PATENT DOCUMENTS

| WO | WO-00 35285 | 6/2000 |
|---|---|---|
| WO | WO 01/10798 A1 | 2/2001 |
| WO | WO-02 096894 | 12/2002 |
| WO | WO 03/000649 A | 1/2003 |
| WO | WO-2004 014368 | 2/2004 |
| WO | WO-2004 072025 | 8/2004 |

OTHER PUBLICATIONS

Vippagunta, Sudha R. "Crystalline Solids." Advanced Drug Delivery Reviews 48(2001): 3-26.*
Lebel, Lorraine A. Dopamine Uptake Inhibitory Activity of Novel Tryptamine 5-HT1 Receptor Ligands. Drug Development Research. 33: 413-421, (1994).*
Matsuura, Izumi. Synthesis of 1H-Imidazoles by the Simple Ring Transformation of 5-Acylaminouracils and 5-Acylaminopyrimidin-4(3H)-ones. J. Chem. Soc. Perkin. Trans. 11, (1991), 2821-2826.*
Database Registry Chemical Abstracts Service, Columbus, Ohio, Accession No. RN 101444-54-6, Entered STN: Apr. 12, 1986.*
Afridi, A.S. et al., "Heterocyclic rearrangements. Part XIV. Attempts to activate ring-opening-ring-closure rearrangements with carbon as the central atom," Journal of the Chemical Society, Perkin Transactions 1, Chemical Society, vol. 3, 1976, pp. 315-320, XP002913844.
Yarovenko, V.N. et al., "Synthesis of Oxamic Acids Thiohydrazides and Carbamoyl1-1,3,4-thiadiazoles," Russian Journal of Organic Chemistry, vol. 39 No. 8, 2003, pp. 1133-1139, XP002341720.
Hirose, Jun-Ichi et al., "Synthesis of 2,3,5-Trisubstituted Furans by the Acid-Catalyzed Decomposition of 1,2-Dioxan-3-ols," Journal of Heterocyclic Chemistry, vol. 31, 1994, pp. 1219-1227, XP002341721.
Yokooji, Aya et al., Palladium-catalyzed direct arylation of thiazoles with aryl bromides, Tetrahedron, vol. 59, 2003, pp. 5685-5689, XP002341722.
Database Crossfire Beilstein, Belstein Institut zur Foerferung der Wissenschaften, Frankfurt am Main, 1992, XP002341744, accession No. 5094531 (BRN) & Andreichov et al., Journal of Organic Chemistry, USSR (English Transl.), 23, 10, 1987; 1994-1996. Summary.
Database Crossfire Beilstein, Beilstein Institut zur Foerderung der Wissenschaften, Frankfurt am Main; 1988, XP002341745, accession No. 22464 (BRN) & Fargher et al., Journal of the Chemical Society, 115, 1919; 1019. Summary.
Database Crossfire Beilstein, Beilstein Institut zur Foerderung der Wissenschaften, Frankfurt am Main; 1997, XP002341746, accession No. 8145947 (BRN) * A.V. Milyutin et al., Pharm. Chem. J. (English Transl.), 31; 1; 1997; 30-33. Summary.
Jansen and Szelke, "Substituted Oxazoles," 1961, pp. 405-411.
Cornforth and Cookson, "Some Reactions of Oxazole-4-carboxylic Acids," 1952 pp. 1085-1088.
Afridi, A. S. et al., "Heterocyclic rearrangements. Part XIV. 1 Attempts to activate ring-opening-ring closure rearrangements with carbon as the central atom," 1976, pp. 315-320.
Andreichov, Y. S. et al., Zhurnal Organischeskoi Khimii, 1987, vol. 23, No. 10, pp. 2254-2255.
Aventis Cropscience GMBH, "4-Haloalkyl-3-heterocyclylpyridines and 4-haloalkyl-5-heterocyclyl-pyrimidines and their use as repellents," Espacenet, Publication Date: Jun. 22, 2000; English Abstract of WO-2000 35285.
BASF AG, "Oxazole carboxylic acid amide or thiazole carboxylic acid amide," Patent Abstracts of Japan, Publication Date: Jun. 20, 1991; English Abstract of JP-03-145478.
Fargher, R. G. et al., Journal of the Chemical Society, Transactions, 1919, vol. 115, pp. 1015-1020.
Hirose, J. et al., "Synthesis of 2,3,5-Trisubstituted furans by the acid-catalyzed decomposition of 1,2-dioxan-3-ols," Journal of Heterocyclic Chemistry, 1994, vol. 31, No. 5, pp. 1219-1227.
Milyutin, A. V. et al., Khimiko-Farmatsevticheskii Zhurnal, 1997, vol. 31, No. 1, pp. 32-35.
Teikoku Hormone MFG Co Ltd., "New 5-substituted isoxazole-3-carboxyamide derivative," Patent Abstract of Japan, Publication Date: Jan. 30, 1996; English Abstract of JP-08 027130.
Yarovenko, V. N. et al., "Synthesis of oxamic acids thiohydrazides and carbamoyl-1,3,4-thiadiazoles," Russian Journal of Organic Chemistry, 2001, vol. 39, No. 8, pp. 1133-1139.
Yokooji, A. et al., "Palladium-catalyzed direct arylation of thiazoles with aryl bromides," Tetrahedron, 2003, vol. 59, pp. 5685-5689.
Thomson Innovation Record View, "Optical brightening of shaped org material by formation," Publication Date: Feb. 18, 1974; English Abstract of JP-49007052.

* cited by examiner

HETEROCYCLIC CARBONYL COMPOUNDS

BACKGROUND OF THE INVENTION

The invention had the object of finding novel compounds having valuable properties, in particular those which can be used for the preparation of medicaments.

The present invention relates to compounds in which the inhibition, regulation and/or modulation of kinase signal transduction, in particular by the cell volume-regulating human kinase h-sgk (human serum and glucocorticoid dependent kinase or SGK), plays a role, furthermore to pharmaceutical compositions which comprise these compounds, and to the use of the compounds for the treatment of SGK-induced diseases.

The SGKs having the isoforms SGK-1, SGK-2 and SGK-3 are a serine/threonine protein kinase family (WO 02/17893).

The compounds according to the invention are preferably selective inhibitors of SGK-1. They may furthermore be inhibitors of SGK-2 and/or SGK-3.

In detail, the present invention relates to compounds which inhibit, regulate and/or modulate signal transduction by SGKs, to compositions which comprise these compounds, and to processes for the use thereof for the treatment of SGM-induced diseases and conditions, such as diabetes (for example diabetes mellitus, diabetic nephropathy, diabetic neuropathy, diabetic angiopathy and microangiopathy), obesity, metabolic syndrome (dyslipidaemia), systemic and pulmonary hypertonia, cardiovascular diseases (for example cardiac fibroses after myocardial infarction, cardiac hypertrophy and cardiac insufficiency, arteriosclerosis) and renal diseases (for example glomerulosclerosis, nephrosclerosis, nephritis, nephropathy, electrolyte excretion disorder), generally in fibroses and inflammatory processes of all types (for example liver cirrhosis, pulmonary fibrosis, fibrosing pancreatitis, rheumatism and arthritis, Crohn's disease, chronic bronchitis, radiation fibrosis, sclerormatitis, cystic fibrosis, scarring, Alzheimer's disease).

The compounds according to the invention can also inhibit the growth of tumour cells and tumour metastases and are therefore suitable for tumour therapy.

The compounds according to the invention are furthermore used for the treatment of coagulopathies, such as, for example, dysfibrinogenaemia, hypoproconvertinaemia, haemophilia B, Stuart-Prower defect, prothrombin complex deficiency, consumption coagulopathy, hyperfibrinolysis, immunocoagulopathy or complex coagulopathies, and also in neuronal excitability, for example epilepsy. The compounds according to the invention can also be employed therapeutically in the treatment of a glaucoma or cataract. The compounds according to the invention are furthermore used in the treatment of bacterial infections and in anti-infectious therapy. The compounds according to the invention can also be employed therapeutically for increasing learning ability and attention. In addition, the compounds according to the invention counter cell ageing and stress and thus increase life expectancy and fitness in the elderly.

The compounds according to the invention are furthermore used in the treatment of tinitus.

The identification of small compounds which specifically inhibit, regulate and/or modulate signal transduction of SGKs is therefore desirable and an aim of the present invention.

It has been found that the compounds according to the invention and salts thereof have very valuable pharmacological properties while being well tolerated.

In particular, they exhibit SGK inhibiting effects.

The present invention therefore relates to compounds according to the invention as medicaments and/or medicament active ingredients in the treatment and/or prophylaxis of the said diseases and to the use of compounds according to the invention for the preparation of a pharmaceutical for the treatment and/or prophylaxis of the said diseases and also to a process for the treatment of the said diseases which comprises the administration of one or more compounds according to the invention to a patient in need of such an administration.

The host or patient may belong to any mammal species, for example a primate species, particularly humans; rodents, including mice, rats and hamsters; rabbits; horses, cows, dogs, cats, etc. Animal models are of interest for experimental investigations, where they provide a model for the treatment of a human disease.

For identification of a signal transduction pathway and for detection of interactions between various signal transduction pathways, various scientists have developed suitable models or model systems, for example cell culture models (for example Khwaja et al., EMBO, 1997, 16, 2783-93) and models of transgenic animals (for example White et al., Oncogene, 2001, 20, 7064-7072). For the determination of certain stages in the signal transduction cascase, interacting compounds can be utilised in order to modulate the signal (for example Stephens et al., Biochemical J., 2000, 351, 95-105). The compounds according to the invention can also be used as reagents for testing kinase-dependent signal transduction pathways in animals and/or cell culture models or in the clinical diseases mentioned in this application.

Measurement of the kinase activity is a technique which is well known to the person skilled in the art. Generic test systems for the determination of the kinase activity using substrates, for example histone (for example Alessi et al., FEBS Lett. 1996, 399, 3, pages 333-338) or the basic myelin protein are described in the literature (for example Campos-González, R. and Glenney, Jr., J. R. 1992, J. Biol. Chem. 267, page 14535).

Various assay systems are available for identification of kinase inhibitors. In the scintillation proximity assay (Sorg et al., J. of Biomolecular Screening, 2002, 7, 11-19) and the flashplate assay, the radioactive phosphorylation of a protein or peptide as substrate using γATP is measured. In the presence of an inhibitory compound, a reduced radioactive signal, or none at all, is detectable. Furthermore, homogeneous time-resolved fluoroescence resonance energy transfer (HTR-FRET) and fluorescence polarisation (FP) technologies are useful as assay methods (Sills et al., J. of Biomolecular Screening, 2002, 191-214).

Other non-radioactive ELISA assay methods use specific phospho anti-bodies (phospho ABs). The phospho AB only binds the phosphorylated substrate. This binding can be detected by chemoluminescence using a second peroxidase-conjugated antisheep antibody (Ross et al., Biochem. J., 2002, 366, 977-981).

PRIOR ART

Aromatically and heteroaromatically substituted amides are described in WO 03/000649 as inhibitors of the plasminogen activator inhibitor. Imidazolecarboxamides as PDE IV inhibitors are known from WO 96/00218. 4-Aminomethyl-2-substituted imidazole derivatives are described in WO 96/16040 as dopamine receptor ligands.

Other oxazole derivatives are known from WO 01/10798. Other 4-substituted oxazoles have been described by Jansen and Szelke in J. Chem. Soc. 405-411 (1961) and by Cornforth and Cookson in J. Chem. Soc. 1085-1088 (1952).

WO 00/62781 describes the use of medicaments comprising inhibitors of cell volume-regulated human kinase H-SGK.

The use of kinase inhibitors in anti-infectious therapy is described by C. Doerig in Cell. Mol. Biol. Lett. Vol. 8, No. 2A, 2003, 524-525.

The use of kinase inhibitors in obesity is described by N. Perrotti in J. Biol. Chem. 2001, March 23; 276(12):9406-9412.

The following references suggest and/or describe the use of SGK inhibitors in disease treatment:

1: Chung E J, Sung Y K, Farooq M, Kim Y, Im S, Tak W Y, Hwang Y J, Kim Y I, Han H S, Kim J C, Kim M K. Gene expression profile analysis in human hepatocellular carcinoma by cDNA microarray. Mol. Cells. 2002; 14:382-7.
2: Brickley D R, Mikosz C A, Hagan C R, Conzen S D. Ubiquitin modification of serum and glucocorticoid-induced protein kinase-1(SGK-1). J Biol. Chem. 2002; 277: 43064-70.
3: Fillon S, Klingel K, Warntges S, Sauter M, Gabrysch S, Pestel S, Tanneur V, Waldegger S, Zipfel A, Viebahn R, Haussinger D, Broer S, Kandolf R, Lang F. Expression of the serine/threonine kinase hSGK1 in chronic viral hepatitis. Cell Physiol Biochem. 2002; 12:47-54.
4: Brunet A, Park J, Tran H, Hu L S, Hemmings B A, Greenberg M E. Protein kinase SGK mediates survival signals by phosphorylating the forkhead transcription factor FKHRL1 (FOXO3a). Mol Cell Biol 2001; 21:952-65
5: Mikosz C A, Brickley D R, Sharkey M S, Moran T W, Conzen S D. Glucocorticoid receptor-mediated protection from apoptosis is associated with induction of the serine/threonine survival kinase gene, sgk-1. J Biol. Chem. 2001; 276:16649-54.
6: Zuo Z, Urban G, Scammell J G, Dean N M, McLean T K, Aragon I, Honkanen R E. Ser/Thr protein phosphatase type 5 (PP5) is a negative regulator of glucocorticoid receptor-mediated growth arrest. Biochemistry. 1999; 38:8849-57.
7: Buse P, Tran S H, Luther E, Phu P T, Aponte G W, Firestone G L. Cell cycle and hormonal control of nuclear-cytoplasmic localisation of the serum- and glucocorticoid-inducible protein kinase, Sgk, in mammary tumour cells. A novel convergence point of anti-proliferative and proliferative cell signalling pathways. J Biol. Chem. 1999; 274:7253-63.
8: M. Hertweck, C. Göbel, R. Baumeister: *C. elegans* SGK-1 is the critical component in the Akt/PKB Kinase complex to control stress response and life span. Developmental Cell, Vol. 6, 577-588, April, 2004.

SUMMARY OF THE INVENTION

The invention relates to compounds of the formula I

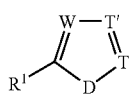

I in which
$R^1$, $R^{1a}$ each, independently of one another, denote a mono- or bicyclic saturated, unsaturated or aromatic carbo- or heterocycle having 0 to 4 N, O and/or S atoms, which may be mono-, di- or trisubstituted by $R^2$, Hal, —[C($R^3_2$)]$_n$—Ar, —[C($R^3$)$_2$]$_n$-Het, $OR^2$, $N(R^2)_2$, $NO_2$, CN, —[C($R^3$)$_2$]$_n$COOR$^2$, —[C($R^3$)$_2$]$_n$CON(R$^2$)$_2$, —[C($R^3$)$_2$]$_n$CONR$^2$N(R$^2$)$_2$, O—[C($R^3$)$_2$]$_o$CON(R$^2$)$_2$, O—[C($R^3$)$_2$]$_o$CONR$^2$N(R$^2$)$_2$, NR$^2$COA, NR$^2$CON(R$^2$)$_2$, NR$^2$SO$_2$A, COR$^2$, SO$_2$NR$^2$, S(O)$_m$A, =S, =NR$^3$ and/or =O (carbonyl oxygen),
D denotes O, NH or S,
W denotes CX or N,
T denotes CX, N or CR,
T' denotes CX, N or CR, with the proviso that one of the radicals T or T' denotes CR$^5$ and the other is not equal to CR,
R denotes —C(=O)—N(R$^2$)[C(R$^2$)$_2$]$_n$R$^{1a}$,
X denotes H, Hal, A, OR$^2$, N(R$^2$)$_2$, NO$_2$, CN, COOR$^2$, CON(R$^2$)$_2$, NR$^2$COA, NR$^2$SO$_2$A, COR$^2$ or SO$_2$NR$^2$,
R$^2$ denotes H, A, —[C(R$^3$)$_2$]$_n$—Ar', —[C(R$^3$)$_2$]$_n$-Het', —[C(R$^3$)$_2$]$_n$-cycloalkyl, —[C(R$^3$)$_2$]—OR$^3$, —[C(R$^3$)$_2$]$_n$—COOA or —[C(R$^3$)$_2$]$_n$N(R$^3$)$_2$,
R$^3$ denotes H or A,
A denotes unbranched or branched alkyl having 1-10 C atoms, in which one or two CH$_2$ groups may be replaced by O or S atoms and/or by —CH=CH— groups and/or in addition 1-7H atoms may be replaced by F,
Ar denotes phenyl, naphthyl or biphenyl, each of which is unsubstituted or mono-, di- or trisubstituted by Hal, A, OR$^2$, N(R$^2$)$_2$, NO$_2$, CN, COOR$^2$, CON(R$^2$)$_2$, NR$^2$COA, NR$^2$CON(R$^2$)$_2$, NR$^2$SO$_2$A, COR$^3$, SO$_2$N(R$^2$)$_2$, S(O)$_m$A, —[C(R$^3$)$_2$]$_n$—COOR$^2$ or —O[C(R$^3$)$_2$]$_o$—COOR$^3$,
Ar' denotes phenyl, naphthyl or biphenyl, each of which is unsubstituted or mono-, di- or trisubstituted by Hal, A, OR$^3$, N(R$^3$)$_2$, NO$_2$, CN, COOR$^3$, CON(R$^3$)$_2$, NR$^3$COA, NR$^3$CON(R$^3$)$_2$, NR$^3$SO$_2$A, COR$^3$, SO$_2$N(R$^3$)$_2$, S(O)$_m$A, —[C(R$^3$)$_2$]$_n$—COOR$^3$ or —O[C(R$^3$)$_2$]$_o$—COOR$^3$,
Het denotes a mono- or bicyclic saturated, unsaturated or aromatic heterocycle having 1 to 4 N, O and/or S atoms, which may be mono-, di- or trisubstituted by Hal, A, —[C(R$^3_2$)]$_n$—Ar, —[C(R$^3$)$_2$]$_n$-Het', —[C(R$^3$)$_2$]$_n$-cycloalkyl, —[C(R$^3$)$_2$]$_n$—OR$^2$, —[C(R$^3$)$_2$]$_n$—N(R$^3$)$_2$, NO$_2$, CN, —[C(R$^3$)$_2$]$_n$COOR$^2$, O—[C(R$^3$)$_2$]$_n$COOR$^2$, —[C(R$^3$)$_2$]$_n$CON(R$^2$)$_2$, —[C(R$^3$)$_2$]$_n$CONR$^2$N(R$^2$)$_2$, O—[C(R$^3$)$_2$]$_o$CON(R$^2$)$_2$, O—[C(R$^3$)$_2$]$_o$CONR$^2$N(R$^2$)$_2$, —[C(R$^3$)$_2$]$_n$—NR$^2$COA, NR$^2$CON(R$^2$)$_2$, —[C(R$^3$)$_2$]$_n$—NR$^2$SO$_2$A, COR$^2$, SO$_2$NR$^2$, S(O)$_m$A, =S, =NR$^2$ and/or =O (carbonyl oxygen),
Het' denotes a mono- or bicyclic saturated, unsaturated or aromatic heterocycle having 1 to 4 N, O and/or S atoms, which may be mono-, di- or trisubstituted by Hal, A, OR$^3$, N(R$^3$)$_2$, NO$_2$, CN, COOR$^3$, CON(R$^3$)$_2$, NR$^3$COA, NR$^3$SO$_2$A, COR$^3$, SO$_2$NR$^3$, S(O)$_m$A, =S, =NR$^3$ and/or =O (carbonyl oxygen),
Hal denotes F, Cl, Br or I,
m denotes 0, 1 or 2,
n denotes 0, 1, 2 or 3,
o denotes 1, 2 or 3,
and pharmaceutically usable derivatives, salts, solvates and stereoisomers thereof, including mixtures thereof in all ratios.

The invention relates to the compounds of the formula I and salts thereof and to a process for the preparation of compounds of the formula I according to claims 1-21 and pharmaceutically usable derivatives, solvates, salts and stereoisomers thereof, characterised in that
a) a compound of the formula I

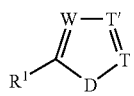

I in which

T denotes CX, N or CR,

T' denotes CX, N or CR, with the proviso that one of the radicals T or T' denotes CR and the other is not equal to CR, R denotes —C(=O)-L, $R^1$, W, D and X have the meanings indicated in claim 1, and L denotes Cl, Br, I or a free or reactively functionally modified OH group, is reacted with a compound of the formula III

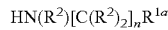     III in which $R^{1a}$, $R^2$ and n have the meanings indicated in claim 1, or b) a radical $R^1$ in a compound of the formula I is converted into another radical $R^1$ by cleaving an ether, and/or a base or acid of the formula I is converted into one of its salts.

The invention also relates to the stereoisomers (E, Z isomers) and the hydrates and solvates of these compounds. Solvates of the compounds are taken to mean adductions of inert solvent molecules onto the compounds which form owing to their mutual attractive force. Solvates are, for example, mono- or dihydrates or alcoholates.

Pharmaceutically usable derivatives is taken to mean, for example, the salts of the compounds according to the invention and also so-called prodrug compounds.

Prodrug derivatives is taken to mean compounds of the formula I which have been modified, with, for example, alkyl or acyl groups, sugars or oligopeptides and which are rapidly cleaved in the organism to form the active compounds according to the invention.

These also include biodegradable polymer derivatives of the compounds according to the invention, as is described, for example, in Int. J. Pharm. 115, 61-67 (1995).

The expression "effective amount" means the amount of a medicament or pharmaceutical active ingredient which causes a biological or medical response which is sought or aimed at, for example by a researcher or physician, in a tissue, system, animal or human.

In addition, the expression "therapeutically effective amount" means an amount which, compared with a corresponding subject who has not received this amount, has the following consequence:

improved treatment, healing, prevention or elimination of a disease, syndrome, condition, complaint, disorder or prevention of side effects or also the reduction in the progress of a disease, condition, disorder or side effects or also the reduction in the progress of a disease, condition or disorder.

The expression "therapeutically effective amount" also encompasses the amounts which are effective for increasing normal physiological function.

The invention also relates to mixtures of the compounds of the formula I according to the invention, for example mixtures of two diastereomers, for example in the ratio 1:1, 1:2, 1:3, 1:4, 1:5, 1:10, 1:100 or 1:1000. These are particularly preferably mixtures of stereoisomeric compounds.

For all radicals which occur more than once, their meanings are independent of one another.

Above and below, the radicals and parameters $R^1$, D, W, T and T' have the meanings indicated for the formula I, unless expressly indicated otherwise.

A denotes alkyl, is unbranched (linear) or branched, and has 1, 2, 3, 4, 5, 6, 7, 8, 9 or 10 C atoms. A preferably denotes methyl, furthermore preferably ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, further preferably, for example, trifluoromethyl.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

Ar denotes, for example, phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino)phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)phenyl, o-, m- or p-cyanophenyl, o-, m- or p-ureidophenyl, o-, m- or p-formylphenyl, o-, m- or p-acetylphenyl, o-, m- or p-aminosulfonylphenyl, o-, m- or p-carboxyphenyl, o-, m- or p-carboxymethylphenyl, o-, m- or p-carboxymethoxyphenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

Ar preferably denotes, for example, phenyl which is unsubstituted or mono-, di- or trisubstituted by Hal, A, $OR^3$, $SO_2A$, $COOR^3$ or CN, very particularly preferably phenyl which is unsubstituted or mono-, di- or trisubstituted by Hal and/or A.

Ar' preferably denotes, for example, phenyl which is unsubstituted or mono-, di- or trisubstituted by Hal, A, $OR^3$, $SO_2A$, $COOR^3$ or CN, very particularly preferably phenyl which is unsubstituted or mono-, di- or trisubstituted by Hal and/or A.

Irrespective of further substitutions, Het denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 2-, 3-, 4-, 5-, 6- or 7-indazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-innolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4- or -5-yl or 2,1,3-benzoxadiazol-5-yl.

The heterocyclic radicals can also be partially or fully hydrogenated. Het can thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, 3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, further preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy) phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl or 2,3-dihydro-2-oxofuranyl.

Het preferably denotes a monocyclic saturated, unsaturated or aromatic heterocycle having 1 to 2 N and/or O atoms, which may be unsubstituted or mono-, di- or trisubstituted by A, Hal, OH and/or OA.

Het particularly preferably denotes a monocyclic saturated heterocycle having 1 to 2 N and/or O atoms, which may be unsubstituted or mono- or disubstituted by A.

In a further embodiment, Het very particularly preferably denotes pyrrolidinyl, piperidinyl, morpholinyl or piperazinyl.

In a further embodiment, Het particularly preferably denotes furyl, thienyl, pyrrolyl, imidazolyl, pyridyl, pyrimidinyl, pyrazolyl, thiazolyl, indolyl, pyrrolidinyl, piperidinyl, morpholinyl or piperazinyl, each of which is unsubstituted or mono-, di- or trisubstituted by A, Hal, OH and/or OA.

Het' preferably denotes a monocyclic saturated, unsaturated or aromatic heterocycle having 1 to 2 N and/or O atoms, which may be unsubstituted or mono-, di- or trisubstituted by A, Hal, OH and/or OA.

Het' particularly preferably denotes a monocyclic saturated heterocycle having 1 to 2 N and/or O atoms, which may be unsubstituted or mono- or disubstituted by A.

In a further embodiment, Het' very particularly preferably denotes pyrrolidinyl, piperidinyl, morpholinyl or piperazinyl.

In a further embodiment, Het' particularly preferably denotes furyl, thienyl, pyrrolyl, imidazolyl, pyridyl, pyrimidinyl, pyrazolyl, thiazolyl, indolyl, pyrrolidinyl, piperidinyl, morpholinyl or piperazinyl, each of which is unsubstituted or mono-, di- or trisubstituted by A, Hal, OH and/or OA.

Mono- or bicyclic saturated, unsaturated or aromatic carbocycle preferably denotes cyclopentyl, cyclopentenyl, cyclohexyl, cyclohexenyl, phenyl or naphthyl, particularly preferably phenyl or naphthyl.

Mono- or bicyclic saturated, unsaturated or aromatic heterocycle denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 2-, 3-, 4-, 5-, 6- or 7-indazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4- or -5-yl or 2,1,3-benzoxadiazol-5-yl, furthermore 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore 2,3-dihydrobenzofuranyl or 2,3-dihydro-2-oxofuranyl.

$R^1$ preferably denotes a mono- or bicyclic unsaturated or aromatic carbo- or heterocycle having 0 to 4 N, O and/or S atoms, which is unsubstituted or is mono-, di- or trisubstituted by A, Hal, $—[C(R^3)_2]_n—OR^3$, $—[C(R^3)_2]_nN(R^3)_2$ or $—[C(R^3)_2]_nCOOR^3$ $R^1$ particularly preferably denotes phenyl, which is unsubstituted or is mono-, di- or trisubstituted by A, Hal, OH or OA, or $R^1$ particularly preferably denotes a mono- or bicyclic unsaturated or aromatic heterocycle having 1-2 nitrogen atoms, such as, for example, 1H-indazole, which is un-substituted or is monosubstituted by $NH_2$.

The compounds of the formula I may have one or more chiral centres and can therefore occur in various stereoisomeric forms. The formula I encompasses all these forms.

Accordingly, the invention relates, in particular, to the compounds of the formula I in which at least one of the said radicals has one of the preferred meanings indicated above. Some preferred groups of compounds may be expressed by the following sub-formulae Ia to Is, which conform to the formula I and in which the radicals not designated in greater detail have the meaning indicated for the formula I, but in which in Ia $R^1$, $R^{1a}$ each, independently of one another, denote a mono- or bicyclic saturated, unsaturated or aromatic carbo- or heterocycle having 0 to 4 N, O and/or S atoms, which is unsubstituted or is mono-, di- or trisubstituted by A, Hal, $NO_2$, CN, $—[C(R^3)_2]_n—Ar'$, $—O—[C(R^3)_2]_n—Ar'$, $—[C(R^3)_2]_n$-Het', $—[C(R^3)_2]_n$-cycloalkyl, $—[C(R^3)_2]_nCON$-HAr', $—[C(R^3)_2]_n—OR^3$, $—[C(R^3)_2]_nN(R^3)_2$, $—[C(R^3)_2]_nCOOR^3$, $[C(R^3)_2]_nCON(R^3)_2$, $—[C(R^3)_2]_nCONR^3N(R^3)_2$, $O—[C(R^3)_2]_oCON(R^3)_2$, O—[C(R³)₂]ₒCONR³N(R³)₂, NR³COA, NR³CON(R³)₂, NR³SO₂A, COR³, SO₂NR³, S(O)ₘA, =S, =NR³ and/or =O (carbonyl oxygen);

in Ib R¹, R¹ᵃ each, independently of one another, denote a mono- or bicyclic saturated, unsaturated or aromatic carbo- or heterocycle having 0 to 4 N, O and/or S atoms, which is unsubstituted or is mono-, di- or trisubstituted by A, Hal, CN, —[C(R³)₂]ₙ—Ar', —O—[C(R³)₂]ₙ—Ar', —C(R³)₂]ₙCONHAr', —[C(R³)₂]ₙ—OR³, —[C(R³)₂]ₙN(R³)₂ or —[C(R³)₂]ₙCOOR³;

in Ic R¹, R¹ᵃ each, independently of one another, denote a mono- or bicyclic saturated, unsaturated or aromatic carbo- or heterocycle having 0 to 4 N, O and/or S atoms, which is unsubstituted or is mono-, di- or trisubstituted by A, Hal, CN, —[C(R³)₂]ₙ—Ar', —O—[C(R³)₂]ₙ—Ar', —C(R³)₂]ₙCONHAr', —[C(R³)₂]ₙ—OR³, —[C(R³)₂]ₙN(R³)₂ or —[C(R³)₂]ₙCOOR³;

in Id R¹ denotes a mono- or bicyclic unsaturated or aromatic carbo- or heterocycle having 0 to 4 N, O and/or S atoms, which is unsubstituted or is mono-, di- or trisubstituted by A, Hal, benzyloxy, —C(R³)₂]ₙCONHAr', —[C(R³)₂]ₙ—OR³, —[C(R³)₂]ₙN(R³)₂ or —[C(R³)₂]ₙCOOR³;

in Ie R¹ denotes a mono- or bicyclic aromatic carbocycle, which is unsubstituted or is mono-, di- or trisubstituted by A, Hal, —[C(R³)₂]ₙ—OR³, —[C(R³)₂]ₙN(R³)₂ or —[C(R³)₂]ₙCOOR³;

in If R¹ denotes a mono- or bicyclic unsaturated or aromatic heterocycle having 1 to 4 N, O and/or S atoms, which is unsubstituted or is mono-, di- or trisubstituted by A, Hal, —C(R³)₂]ₙCONHAr', —[C(R³)₂]ₙ—OR³, —[C(R³)₂]NO(R³)₂ or —[C(R³)₂]ₙCOOR³;

in Ig R¹ denotes phenyl, which is unsubstituted or mono-, di- or trisubstituted by A, Hal, OH or OA, or a mono- or bicyclic unsaturated or aromatic heterocycle having 1-2 nitrogen atoms, which is unsubstituted or monosubstituted by NH₂;

in Ih R¹ᵃ denotes a monocyclic saturated, unsaturated or aromatic carbocycle, which is unsubstituted or is mono-, di- or trisubstituted by A, Hal, CN, —[C(R³)₂]ₙ—Ar', —O—[C(R¹³)₂]ₙ—Ar', —[C(R³)₂]ₙ—OR³, —[C(R³)₂]ₙN(R³)₂ or —[C(R³)₂]ₙCOOR³;

in Ii R¹ᵃ denotes phenyl, which is unsubstituted or is mono-, di- or trisubstituted by A, Hal, benzyloxy, OH or OA;

in Ij R¹ᵃ denotes phenyl, which is unsubstituted or is mono-, di- or trisubstituted by A, Hal, benzyloxy, OH or OA, or 2,1,3-benzothiadiazole;

in Ik Ar' denotes phenyl, which is unsubstituted or mono-, di- or trisubstituted by Hal and/or A;

in Il Het' denotes a monocyclic saturated, unsaturated or aromatic heterocycle having 1 to 2 N and/or O atoms, which may be unsubstituted or mono-, di- or trisubstituted by A, Hal, OH and/or OA;

in Im Het' denote furyl, thienyl, pyrrolyl, imidazolyl, pyridyl, pyrimidinyl, pyrazolyl, thiazolyl, indolyl, pyrrolidinyl, piperidinyl, morpholinyl or piperazinyl, each of which is unsubstituted or mono-, di- or trisubstituted by A, Hal, OH and/or OA;

in In A denotes unbranched or branched alkyl having 1-6 C atoms, in which 1-7H atoms may be replaced by F;

in Io X denotes H;

in Ip R denotes —C(=O)—N(R³)[C(R³)₂]ₙR¹ᵃ;

in Iq R denotes —C(=O)—NHCH₂R¹ᵃ;

in Ir R¹, R¹ᵃ each, independently of one another, denote a mono- or bicyclic saturated, unsaturated or aromatic carbo- or heterocycle having 0 to 4 N, O and/or S atoms, which is unsubstituted or is mono-, di- or trisubstituted by A, Hal, CN, —[C(R³)₂]ₙ—Ar', —O—[C(R³)₂]ₙ—Ar', —[C(R³)₂]ₙ—OR³, —C(R³)₂]ₙCONHAr', —[C(R³)₂]ₙN(R³)₂ or —[C(R³)₂]ₙCOOR³, D denotes O, NH or S, W denotes CX or N, T denotes CX, N or CR, T' denotes CX, N or CR, with the proviso that one of the radicals T or T' denotes CR and the other is not equal to CR, R denotes —C(=O)—N(R³)[C(R³)₂]ₙR¹ᵃ, X denotes H, R³ denotes H or A, A denotes unbranched or branched alkyl having 1-10 C atoms, in which one or two CH₂ groups may be replaced by O or S atoms and/or by —CH=CH— groups and/or in addition 1-7H atoms may be replaced by F, Ar' denotes phenyl, which is unsubstituted or mono-, di- or trisubstituted by Hal and/or A, Hal denotes F, Cl, Br or I, n denotes 0, 1, 2 or 3;

in Is R¹ denotes a mono- or bicyclic unsaturated or aromatic heterocycle having 1 to 4 N, O and/or S atoms, which is unsubstituted or is mono-, di- or trisubstituted by A, Hal, —C(R³)₂]ₙCONHAr', —[C(R³)₂]ₙ—OR³, —[C(R³)₂]ₙN(R³)₂ or —[C(R³)₂]ₙCOOR³, R¹ᵃ denotes phenyl, which is unsubstituted or is mono-, di- or trisubstituted by A, Hal, benzyloxy, OH or OA, or 2,1,3-benzothiadiazole, D denotes O, NH or S, W denotes CX or N, T denotes CX, N or CR, T' denotes CX, N or CR, with the proviso that one of the radicals T or T' denotes CR and the other is not equal to CR, R denotes —C(=O)—NH—CHA-R¹ᵃ, X denotes H, R³ denotes H or A, Ar denotes phenyl which is unsubstituted or mono-, di- or trisubstituted by Hal and/or A, A denotes unbranched or branched alkyl having 1-10 C atoms, in which one or two CH₂ groups may be replaced by O or S atoms and/or by —CH=CH— groups and/or in addition 1-7H atoms may be replaced by F, Hal denotes F, Cl, Br or I, n denotes 0, 1; 2 or 3;

and pharmaceutically usable derivatives, solvates, salts and stereoisomers thereof, including mixtures thereof in all ratios.

The compounds according to the invention and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se, which are not mentioned here in greater detail.

If desired, the starting materials can also be formed in situ so that they are not isolated from the reaction mixture, but instead are immediately converted further into the compounds according to the invention.

The starting compounds are generally known. If they are novel, however, they can be prepared by methods known per se.

Compounds of the formula I can preferably be obtained by reacting a compound of the formula I

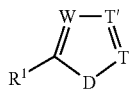

in which
T denotes CX, N or CR,
T' denotes CX, N or CR, with the proviso that one of the radicals T or T' denotes CR and the other is not equal to CR,
R denotes —C(=O)-L,
$R^1$, W, D and X have the meanings indicated in claim 1, and
L denotes Cl, Br, I or a free or reactively functionally modified OH group,
with a compound of the formula III.

The reaction is carried out by methods which are known to the person skilled in the art.

The reaction is generally carried out in an inert solvent, in the presence of an acid-binding agent, preferably an organic base, such as DIPEA, triethylamine, dimethylaniline, pyridine or quinoline.

The addition of an alkali or alkaline earth metal hydroxide, carbonate or bicarbonate or of another salt of a weak acid of the alkali or alkaline earth metals, preferably of potassium, sodium, calcium or caesium, may also be favourable.

Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Depending on the conditions used, the reaction time is between a few minutes and 14 days, the reaction temperature is between about −30° and 140°, normally between −10° and 110°, in particular between about 20° and about 100°.

L preferably denotes Cl, Br, I or a free or reactively modified OH group, such as, for example, an activated ester, an imidazolide or alkylsulfonyloxy having 1-6 C atoms (preferably methylsulfonyloxy or trifluoromethylsulfonyloxy) or arylsulfonyloxy having 6-10 C atoms (preferably phenyl- or p-tolylsulfonyloxy). Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart;).

Activated esters are advantageously formed in situ, for example by addition of HOBt or N-hydroxysuccinimide.

The cleavage of an ether is carried out using methods as are known to the person skilled in the art.

Hydrogenolytically removable protective groups (for example benzyl) can be cleaved off by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 1000 and pressures between about 1 and 200 bar, preferably at 20-30° and 1-10 bar.

Another standard method of ether cleavage is the use of boron tribromide.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminum salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminum, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)methylamine (tromethamine), but this is not intended to represent a restriction.

Compounds of the present invention which contain basic nitrogen-containing groups can be quaternised using agents such as ($C_1$-$C_4$)alkyl halides, for example methyl, ethyl, isopropyl and tert-butyl chloride, bromide and iodide; di($C_1$-$C_4$) alkyl sulfates, for example dimethyl, diethyl and diamyl sulfate; ($C_{10}$-$C_{18}$)alkyl halides, for example decyl, dodecyl, lauryl, myristyl and stearyl chloride, bromide and iodide; and aryl($C_1$-$C_4$)alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Compounds of the formula I according to the invention may be chiral owing to their molecular structure and may accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

The invention furthermore relates to the use of the compounds and/or physiologically acceptable salts thereof for the preparation of a medicament (pharmaceutical composition), in particular by non-chemical methods. They can be converted into a suitable dosage form here together with at least one solid, liquid and/or semi-liquid excipient or adjuvant and, if desired, in combination with one or more further active ingredients.

The invention furthermore relates to medicaments comprising at least one compound according to the invention and/or pharmaceutically usable derivatives, solvates and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the disease condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinyl pyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compounds. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds according to the invention and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds according to the invention and the salts, solvates and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the present invention depends on a number of factors, including, for example, the age and weight of the human or animal, the precise disease condition which requires treatment, and its severity, the nature of the formulation and the method of administration, and is ultimately determined by the treating doctor or vet. However, an effective amount of a compound according to the invention is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention furthermore relates to medicaments comprising at least one compound according to the invention and/or pharmaceutically usable derivatives, solvates and stereoisomers thereof, including mixtures thereof in all ratios, and at least one further medicament active ingredient.

The invention also relates to a set (kit) consisting of separate packs of (a) an effective amount of a compound according to the invention and/or pharmaceutically usable derivatives, solvates and stereoisomers thereof, including mixtures thereof in all ratios, and (b) an effective amount of a further medicament active ingredient.

The set comprises suitable containers, such as boxes, individual bottles, bags or ampoules. The set may, for example, comprise separate ampoules, each containing an effective amount of a compound according to the invention and/or pharmaceutically usable derivatives, solvates and stereoisomers thereof, including mixtures thereof in all ratios, and an effective amount of a further medicament active ingredient in dissolved or lyophilised form.

Use

The present compounds are suitable as pharmaceutical active ingredients for mammals, in particular for humans, in the treatment of SGK-induced diseases.

The invention thus relates to the use of compounds according to claim 1 and to pharmaceutically usable derivatives, solvates and stereoisomers, including mixtures thereof in all ratios, for the preparation of a medicament for the treatment of diseases in which the inhibition, regulation and/or modulation of kinase signal transduction plays a role.

Preference is given here to SGK.

Preference is given to the use of compounds according to claim 1 and pharmaceutically usable derivatives, solvates and stereoisomers thereof, including mixtures thereof in all ratios, for the preparation of a medicament for the treatment of diseases which are influenced by inhibition of SGKs by the compounds according to claim 1.

The present invention encompasses the use of the compounds according to claim 1 according to the invention and/or physiologically acceptable salts and solvates thereof for the preparation of a medicament for the treatment or prevention of diabetes (for example diabetes mellitus, diabetic nephropathy, diabetic neuropathy, diabetic angiopathy and microangiopathy), obesity, metabolic syndrome (dyslipidaemia), systemic and pulmonary hypertonia, cardiovascular diseases (for example cardial fibroses after myocardial infarction, cardiac hypertrophy and cardiac insufficiency, arteriosclerosis) and renal diseases (for example glomerulosclerosis, nephrosclerosis, nephritis, nephropathy, electrolyte excretion disorder), generally in fibroses and inflammatory processes of all types (for example liver cirrhosis, pulmonary fibrosis, fibrosing pancreatitis, rheumatism and arthritis, Crohn's disease, chronic bronchitis, radiation fibrosis, sclerormatitis, cystic fibrosis, scarring, Alzheimer's disease). The compounds according to the invention can also inhibit the growth of cancer, tumour cells and tumour metastases and are therefore suitable for tumour therapy. The compounds according to the invention are furthermore used for the treatment of coagulopathies, such as, for example, dysfibrinogenaemia, hypoproconvertinaemia, haemophilia B, Stuart-Prower defect, prothrombin complex deficiency, consumption coagulopathy, hyperfibrinolysis, immunocoagulopathy or complex coagulopathies, and also in neuronal excitability, for example epilepsy. The compounds according to the invention can also be employed therapeutically in the treatment of a glaucoma or cataract. The compounds according to the invention are furthermore used in the treatment of bacterial infections and in anti-infectious therapy. The compounds according to the invention can also be employed therapeutically for increasing learning ability and attention.

Preference is given to the use of compounds according to claim 1 and pharmaceutically usable derivatives, solvates and stereoisomers thereof, including mixtures thereof in all ratios, for the preparation of a medicament for the treatment or prevention of diabetes, obesity, metabolic syndrome (dyslipidaemia), systemic and pulmonary hypertonia, cardiovascular diseases and renal diseases, generally in fibroses and inflammatory processes of all types, cancer, tumour cells, tumour metastases, coagulopathies, neuronal excitability, glaucoma, cataract, bacterial infections and in anti-infectious therapy, for increasing learning ability and attention, and for the treatment and prophylaxis of cell ageing and stress.

Diabetes is preferably diabetes mellitus, diabetic nephropathy, diabetic neuropathy, diabetic angiopathy and microangiopathy.

Cardiovascular diseases are preferably cardial fibroses after myocardial infarction, cardiac hypertrophy, cardiac insufficiency and arteriosclerosis.

Renal diseases are preferably glomerulosclerosis, nephrosclerosis, nephritis, nephropathy and electrolyte excretion disorders.

fibroses and inflammatory processes are preferably liver cirrhosis, pulmonary fibrosis, fibrosing pancreatitis, rheumatism and arthritis, Crohn's disease, chronic bronchitis, radiation fibrosis, sclerormatitis, cystic fibrosis, scarring, Alzheimer's disease.

The invention furthermore relates to the intermediate compounds of the formula I-I

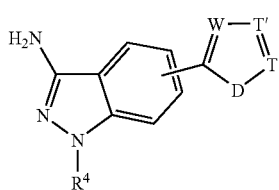

in which
D denotes O, NH or S,
W denotes CX or N,
T denotes CX, N or CR,
T' denotes CX, N or CR, with the proviso that one of the radicals T or T' denotes CR and the other is not equal to CR,
R denotes COOH,
X denotes H,
$R^4$ denotes $R^2$, —$[C(R^3)_2]_n$CON$(R^2)_2$, COR$^2$ or S(O)$_m$A, $R^2$ denotes H, A, —$[C(R^3)_2]_n$—Ar', —$[C(R^3)_2]_n$-Het', —[C(R$^3)_2]_n$-cycloalkyl, —$[C(R^3)_2]_2$OR$^3$, —$[C(R^3)_2]_n$—COOA or —$[C(R^3)_2]_n$N(R$^3)_2$,
$R^3$ denotes H or A,
A denotes unbranched or branched alkyl having 1-10 C atoms, in which one or two CH$_2$ groups may be replaced by O or S atoms and/or by —CH=CH— groups and/or in addition 1-7H atoms may be replaced by F,
Ar' denotes phenyl, which is unsubstituted or mono-, di- or trisubstituted by Hal and/or A,
Het' denotes a monocyclic saturated, unsaturated or aromatic heterocycle having 1 to 2 N and/or O, which may be unsubstituted or mono-, di- or trisubstituted by A, Hal, OH and/or OA,
Hal denotes F, Cl, Br or I,
m denotes 0, 1 or 2,
n denotes 0, 1, 2 or 3,
and/or pharmaceutically usable derivatives, salts, solvates and stereoisomers thereof, including mixtures thereof in all ratios.

Preference is given to intermediate compounds of the formula I-I in which
D denotes O, NH or S,
W denotes CX or N,
T denotes CX, N or CR,
T' denotes CX, N or CR,
with the proviso that one of the radicals T or T' denotes CR and the other is not equal to CR,
R denotes COOH,
X denotes H,
$R^4$ denotes $R^2$, —$[C(R^3)_2]_n$CON$(R^2)_2$, COR$^2$ or S(O)$_m$A,
$R^2$ denotes H, A, —$[C(R^3)_2]_n$—Ar', —$[C(R^3)_2]_n$—OR$^3$, —$[C(R^3)_2]_n$—COOA or —$[C(R^3)_2]_n$N(R$^3)_2$,
$R^3$ denotes H or A,
A denotes unbranched or branched alkyl having 1-10 C atoms, and in addition 1-7H atoms may be replaced by F,
Ar' denotes phenyl, which is unsubstituted or mono-, di- or trisubstituted by Hal and/or A,
Hal denotes F, Cl, Br or I,
m denotes 0, 1 or 2,
n denotes 0, 1, 2 or 3,
and/or pharmaceutically usable derivatives, salts, solvates and stereoisomers thereof, including mixtures thereof in all ratios.

Particular preference is given to intermediate compounds of the formula I-I in which
D denotes O, NH or S,
W denotes CX or N,
T denotes CX, N or CR,
T' denotes CX, N or CR,
with the proviso that one of the radicals T or T' denotes CR and the other is not equal to CR,
R denotes COOH,
X denotes H,
$R^4$ denotes $R^2$ or —$(CH_2)_n$CONHR$^2$,
$R^2$ denotes H, A or —$(CH_2)_n$—Ar',
A denotes unbranched or branched alkyl having 1-10 C atoms, and in addition 1-7H atoms may be replaced by F,
Ar' denotes phenyl, which is unsubstituted or mono-, di- or trisubstituted by Hal and/or A,
Hal denotes F, Cl, Br or I,
n denotes 0, 1, 2 or 3,
and/or pharmaceutically usable derivatives, salts, solvates and stereoisomers thereof, including mixtures thereof in all ratios.

The invention furthermore relates to the intermediate compounds selected from the group
2-(3-amino-1H-indazol-5-yl)-3H-imidazole-4-carboxylic acid ("58"),
2-(3-amino-1H-indazol-5-yl)oxazole-4-carboxylic acid ("59"),
5-(3-amino-1H-indazol-5-yl)furan-2-carboxylic acid ("60"), 5-(3-amino-1-p-tolylcarbamoyl-1H-indazol-5-yl)furan-2-carboxylic acid ("86"),
5-(3-amino-1-benzyl-1H-indazol-5-yl)furan-2-carboxylic acid ("87"),
5-(3-amino-1-methyl-1H-indazol-5-yl)furan-2-carboxylic acid ("88"),
and/or pharmaceutically usable derivatives, salts, solvates and stereoisomers thereof, including mixtures thereof in all ratios.

The invention also relates to medicaments comprising at least one compound of the formula I-I and/or pharmaceutically usable derivatives, salts, solvates and stereoisomers thereof, including mixtures thereof in all ratios, and optionally excipients and/or adjuvants.

The invention also relates to the use of the compounds of the formula I-I and pharmaceutically usable derivatives, salts, solvates and stereoisomers thereof, including mixtures thereof in all ratios, for the preparation of a medicament for the treatment and/or prophylaxis of diseases in which the inhibition, regulation and/or modulation of kinase signal transduction plays a role. The kinases are preferably SGK.

Preference is furthermore given to the use of the compounds "51", "58", "59", "60", and pharmaceutically usable derivatives, solvates and stereoisomers thereof, including mixtures thereof in all ratios, for the preparation of a medicament for the treatment of diseases which are influenced by inhibition of SGK by the said compounds.

Particular preference is given to the use for the preparation of a medicament for the treatment or prevention of diabetes, obesity, metabolic syndrome (dyslipidaemia), systemic and pulmonary hypertonia, cardiovascular diseases and kidney diseases, generally in fibroses and inflammatory processes of all types, cancer, tumour cells, tumour metastases, coagulopathies, neuronal excitability, glaucoma, cataracts, bacterial infections and in anti-infectious therapy, for increasing learning ability and attention, and for the treatment and prophylaxis of cell ageing and stress.

Assays

The compounds according to the invention described in the examples were tested in the assays described below and were found to have kinase-inhibitory activity. Further assays are known from the literature and could easily be performed by the person skilled in the art (see, for example, Dhanabal et al., Cancer Res. 59:189-197; Xin et al., J. Biol. Chem. 274:9116-9121; Sheu et al., Anticancer Res. 18:4435-4441; Ausprunk et al., Dev. Biol. 38:237-248; Gimbrone et al., J. Natl. Cancer Inst. 52:413-427; Nicosia et al., In Vitro 18:538-549).

Above and below, all temperatures are indicated in °C. In the following examples, "conventional work-up" means: if necessary, water is added, the pH is adjusted, if necessary, to between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation. Rf values on silica gel; eluent: ethyl acetate/methanol 9:1.

Mass spectrometry (MS):
EI (electron impact ionisation) $M^+$
FAB (fast atom bombardment) $(M+H)^+$
ESI (electrospray ionisation) $(M+H)^+$ (unless indicated otherwise)

EXAMPLE 1

The preparation of N-3-hydroxybenzyl-2-(4-hydroxyphenyl)-3H-imidazole-4-carboxamide ("1") is carried out analogously to the following scheme:

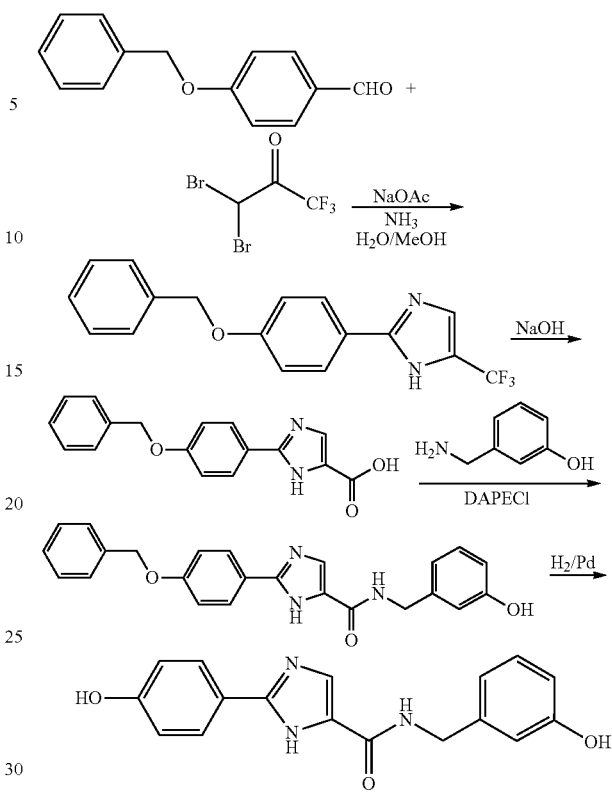

1.1 6.75 g (25.0 mmol) of 1,1-dibromo-3,3,3-trifluoroacetone are mixed with 28 ml of water, and 6.80 g (50.0 mmol) of sodium acetate trihydrate are added. This solution is heated to 90° C. and added in one portion to a previously prepared suspension of 5.31 g (25.0 mmol) of 4-benzyloxybenzaldehyde in 130 ml of methanol and 35 ml of conc. ammonia. The reaction mixture is stirred at room temperature for 40 hours. It is concentrated to a volume of about 70 ml, and the precipitate formed is filtered off: 2-(4-benzyloxyphenyl)-5-trifluoromethyl-1H-imidazole as slightly yellowish solid; ESI 319.

1.2 30 ml of 2.5 N aqueous NaOH are added to a solution of 1.00 g (3.14 mmol) of 2-(4-benzyloxyphenyl)-5-trifluoromethyl-1H-imidazole in 20 ml of methanol, and the mixture is refluxed for 3 hours. The reaction mixture is allowed to cool and is acidified using conc. hydrochloric acid. The precipitate formed is filtered off and dried: 2-(4-benzyloxyphenyl)-3H-imidazole-4-carboxylic acid as colourless solid; ESI 295.

1.3 403 mg (2.1 mmol) of N-(3-dimethylaminopropyl)-N'-ethylcarbodiimide hydrochloride (DAPECI) are added to a solution of 447 mg (1.62 mmol) of 2-(4-benzyloxyphenyl)-3H-imidazole-4-carboxylic acid and 200 mg (1.62 mmol) of 3-hydroxybenzylamine in 1 ml of DMF, and the mixture is stirred at room temperature for 18 hours. The reaction mixture is added to water, and the precipitate formed is filtered off: N-3-hydroxybenzyl-2-(4-benzyloxyphenyl)-3H-imidazole-4-carboxamide as colourless solid; ESI 400.

1.4 440 mg of water-moist palladium on active carbon (5% of Pd) are added to a solution of 440 mg (1.10 mmol) of N-3-hydroxybenzyl-2-(4-benzyloxyphenyl)-3H-imidazole-4-carboxamide in a mixture of 10 ml of methanol and 5 ml of THF, and the mixture is hydrogenated at room temperature and atmospheric pressure for 17 hours. The catalyst is filtered off, and the filtrate is evaporated: N-3-hydroxybenzyl-2-(4-hydroxyphenyl)-3H-imidazole-4-carboxamide ("1") as colourless solid; ESI 310.

An analogous procedure gives

N-3-hydroxybenzyl-2-(2,4-dihydroxyphenyl)-3H-imidazole-4-carboxamide ("6"), ESI 326;

N-4-hydroxyphenyl-2-(4-hydroxyphenyl)-3H-imidazole-4-carboxamide ("9"), ESI 296;

N-3-hydroxyphenyl-2-(3-hydroxyphenyl)-3H-imidazole-4-carboxamide ("10"), ESI 296;

N-4-hydroxyphenyl-2-(3-hydroxyphenyl)-3H-imidazole-4-carboxamide ("11"), ESI 296;

N-3-hydroxyphenyl-2-(4-hydroxyphenyl)-3H-imidazole-4-carboxamide ("12"), ESI 296;

N-3-hydroxybenzyl-2-(4-hydroxy-2-methylphenyl)-3H-imidazole-4-carboxamide ("16"), ESI 324;

N-3-fluorobenzyl-2-(4-hydroxyphenyl)-3H-imidazole-4-carboxamide ("20"), ESI 312;

N-4-hydroxybenzyl-2-(4-hydroxyphenyl)-3H-imidazole-4-carboxamide ("21"), ESI 310;

N-4-hydroxybenzyl-2-(3-hydroxyphenyl)-3H-imidazole-4-carboxamide ("23"), ESI 310;

N-3-hydroxybenzyl-2-(3-hydroxyphenyl)-3H-imidazole-4-carboxamide ("26"), ESI 310;

N-3-fluorobenzyl-2-(3-hydroxyphenyl)-3H-imidazole-4-carboxamide ("27"), ESI 312;

N-2-methoxybenzyl-2-(4-hydroxyphenyl)-3H-imidazole-4-carboxamide ("31"), ESI 324.

An analogous procedure to the preparation of products 1.1-1.3 gives

N-3-fluorobenzyl-2-(4-fluorophenyl)-3H-imidazole-4-carboxamide ("28"), ESI 314;

N-3-hydroxybenzyl-2-(4-fluorophenyl)-3H-imidazole-4-carboxamide ("29"), ESI 312;

N-3-hydroxybenzyl-2-(3-bromophenyl)-3H-imidazole-4-carboxamide ("52"), ESI 372, 374;

N-3-methoxybenzyl-2-(3-bromophenyl)-3H-imidazole-4-carboxamide ("53"), ESI 386, 388;

N-3-chlorobenzyl-2-(3-bromophenyl)-3H-imidazole-4-carboxamide ("54"), ESI 392;

N-3-hydroxybenzyl-2-(3-chlorophenyl)-3H-imidazole-4-carboxamide ("55"), ESI 328;

N-3-methoxybenzyl-2-(3-chlorophenyl)-3H-imidazole-4-carboxamide ("56"), ESI 342;

N-3-chlorobenzyl-2-(3-chlorophenyl)-3H-imidazole-4-carboxamide ("57"), ESI 346.

EXAMPLE 2

The preparation of N-3-hydroxybenzyl-2-(3-hydroxyphenyl)oxazole-4-carboxamide ("2") is carried out analogously to the following scheme:

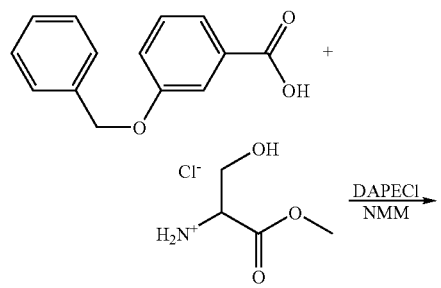

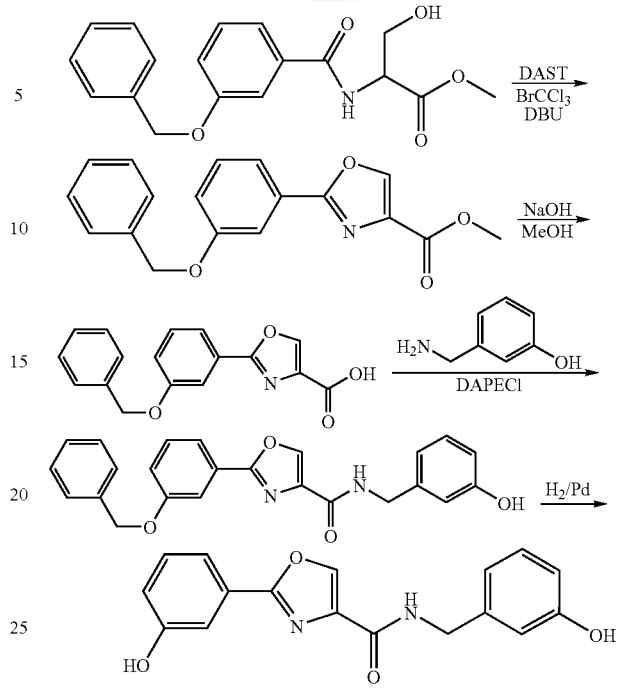

2.1 1.60 g (8.38 mmol) of N-(3-dimethylaminopropyl)-N'-ethylcarbodiimide hydrochloride (DAPECI) and 0.72 ml of N-methylmorpholine are added to a solution of 1.47 g (6.44 mmol) of 3-benzyloxybenzoic acid and 1.00 g (6.43 mmol) of D/L-serine methyl ester hydrochloride in 5 ml of DMF, and the mixture is stirred at room temperature for 18 hours. The reaction mixture is added to water, and the precipitate formed is filtered off: methyl 2-(3-benzyloxybenzoylamino)-3-hydroxypropionate as colourless solid; ESI 330.

2.2 A solution of 1.85 g (5.62 mmol) of methyl 2-(3-benzyloxybenzoylamino)-3-hydroxypropionate in 50 ml of dichloromethane is cooled to −20° C. in an acetone/dry ice bath, and 990 mg (6.14 mmol) of diethylaminosulfur trifluoride (DAST) are added dropwise. The mixture is stirred at this temperature for 30 minutes, and 3.97 g (20.0 mmol) of bromotrichloromethane and 3.08 g (20.2 mmol) of 1,8-diazabicyclo[5.4.0]undec-7-ene (DBU) are then added dropwise. The reaction mixture is stirred at 0° C. for 7 hours, and saturated sodium hydrogencarbonate solution is then added. The organic phase is separated off, and the aqueous phase is extracted with ethyl acetate. The combined organic phase are evaporated and chromatographed on a silica-gel column using petroleum ether/ethyl acetate: methyl 2-(3-benzyloxyphenyl)oxazole-4-carboxylate as colourless solid; ESI 310.

2.3 7.4 ml of 1 N aqueous NaOH are added to a solution of 1.90 g (6.14 mmol) of methyl 2-(3-benzyloxyphenyl)oxazole-4-carboxylate in 20 ml of methanol, and the mixture is stirred at room temperature for 18 hours. The reaction mixture is concentrated to a volume of about 7 ml, acidified using conc. hydrochloric acid and extracted with ethyl acetate. The organic phase is dried over sodium sulfate and evaporated: 2-(3-benzyloxyphenyl)oxazole-4-carboxylic acid as colourless solid; ESI 296.

2.4 126 mg (0.66 mmol) of DAPECI are added to a solution of 150 mg (0.51 mmol) of 2-(3-benzyloxyphenyl)oxazole-4-carboxylic acid and 63 mg (0.51 mmol) of 3-hydroxybenzylamine in 1 ml of DMF, and the mixture is stirred at room temperature for 18 hours. The reaction mixture is added to water, and the precipitate formed is filtered off: N-3-hydroxybenzyl-2-(3-benzyloxyphenyl)oxazole-4-carboxamide as colourless solid; ESI 401.

2.5 150 mg of water-moist palladium on active carbon (5% of Pd) are added to a solution of 75 mg (0.19 mmol) of N-3-hydroxybenzyl-2-(3-benzyloxyphenyl)oxazole-4-carboxamide in 10 ml of methanol, and the mixture is hydrogenated at room temperature and atmospheric pressure for 17 hours. The catalyst is filtered off, and the filtrate is evaporated: N-3-hydroxybenzyl-2-(3-hydroxyphenyl)oxazole-4-carboxamide ("2") as colourless solid; ESI 311.

An analogous procedure gives
N-3-hydroxybenzyl-2-(4-hydroxyphenyl)oxazole-4-carboxamide ("7"), ESI 311;
N—[(R)-1-(3-hydroxyphenyl)ethyl]-2-(3-hydroxyphenyl)oxazole-4-carboxamide ("8"), ESI 325;
N-3-hydroxyphenyl-2-(3-hydroxyphenyl)oxazole-4-carboxamide ("13"), ESI 297;
N-4-hydroxybenzyl-2-(3-hydroxyphenyl)oxazole-4-carboxamide ("14"), ESI 311;
N-4-hydroxyphenyl-2-(3-hydroxyphenyl)oxazole-4-carboxamide ("15"), ESI 297;
N-3-fluorobenzyl-2-(3-hydroxyphenyl)oxazole-4-carboxamide ("24"), ESI 313;
N—[(S)-1-(3-hydroxyphenyl)ethyl]-2-(3-hydroxyphenyl)oxazole-4-carboxamide ("25"), ESI 325;
N-3-fluorobenzyl-2-(4-hydroxyphenyl)oxazole-4-carboxamide ("30"), ESI 313;
N-3,5-difluorobenzyl-2-(3-hydroxyphenyl)oxazole-4-carboxamide ("44"), ESI 331;
N-2-methoxybenzyl-2-(3-hydroxyphenyl)oxazole-4-carboxamide ("45a"), ESI 325.
N-2-methoxybenzyl-2-(4-hydroxyphenyl)oxazole-4-carboxamide ("45"), ESI 325.

The following compounds are obtained analogously to the preparation of products 2.1-2.4
N-3-fluorobenzyl-2-(3-chloro-6-methoxyphenyl)oxazole-4-carboxamide ("34"), ESI 361;
N-3-hydroxybenzyl-2-(3-chloro-6-methoxyphenyl)oxazole-4-carboxamide ("46"), ESI 359;
N—[(S)-1-(3-hydroxyphenyl)ethyl]-2-(3-chloro-6-methoxyphenyl)oxazole-4-carboxamide ("47"), ESI 373;
N—[(R)-1-(3-hydroxyphenyl)ethyl]-2-(3-chloro-6-methoxyphenyl)oxazole-4-carboxamide ("48"), ESI 373;
N-3-methoxybenzyl-2-(3-chloro-6-methoxyphenyl)oxazole-4-carboxamide ("49"), ESI 373.

EXAMPLE 3

The preparation of N-3-hydroxybenzyl-5-(4-hydroxyphenyl)furan-2-carboxamide ("3") is carried out analogously to the following scheme:

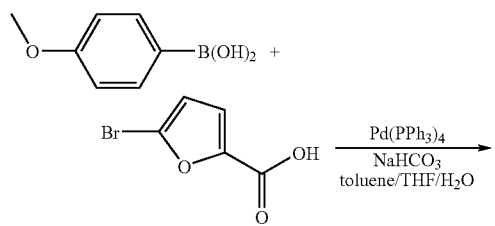

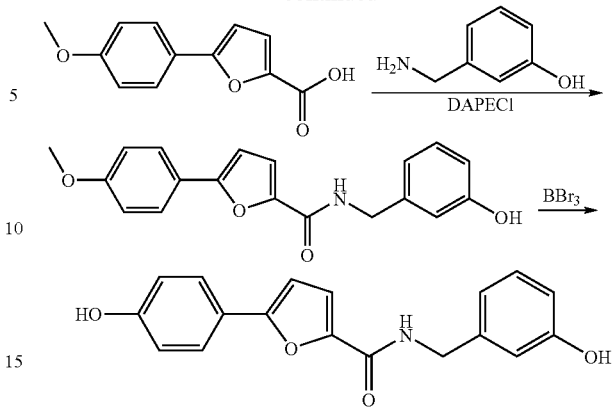

3.1 6.90 g (36.1 mmol) of 5-bromofuran-2-carboxylic acid, 1.10 g (0.952 mmol) of tetrakis(triphenylphosphine)palladium and a solution of 5.5 g (65 mmol) of sodium hydrogencarbonate in 50 ml of water are added successively to a suspension of 5.00 g (32.9 mmol) of 4-methoxybenzeneboronic acid in a mixture of 50 ml of toluene and 30 ml of THF. The reaction mixture is refluxed for 3 hours with vigorous stirring. The mixture is allowed to cool, ethyl acetate and sodium hydrogencarbonate solution are added, and the aqueous phase is separated off. The latter is acidified using 1 N hydrochloric acid, and the precipitate formed is filtered off and dried: 5-(4-methoxyphenyl)furan-2-carboxylic acid as colourless solid; ESI 219.

3.2 454 mg (2.38 mmol) of N-(3-dimethylaminopropyl)-N'-ethylcarbodiimide hydrochloride (DAPECI) are added to a solution of 400 mg (1.83 mmol) of 5-(4-methoxyphenyl)furan-2-carboxylic acid and 226 mg (1.84 mmol) of 3-hydroxybenzylamine in 2 ml of DMF, and the mixture is stirred at room temperature for 18 hours. The reaction mixture is added to water, and the precipitate formed is filtered off: N-3-hydroxybenzyl-5-(4-methoxyphenyl)furan-2-carboxamide ("22") as colourless solid; ESI 324.

3.3 130 µl of boron tribromide are added to a solution of 150 mg (0.464 mmol) of N-3-hydroxybenzyl-5-(4-methoxyphenyl)furan-2-carboxamide in 5 ml of dichloromethane, and the mixture is stirred at room temperature for 18 hours. 3 ml of methanol are slowly added dropwise to the reaction. The reaction mixture is evaporated, methanol is added to the residue, the mixture is stirred for 10 minutes and re-evaporated: N-3-hydroxybenzyl-5-(4-hydroxyphenyl)furan-2-carboxamide ("3") as colourless solid; ESI 310.

An analogous procedure to the preparation of products 3.1-3.2 gives
N-3-hydroxybenzyl-5-(3-chlorophenyl)furan-2-carboxamide ("17"), ESI 328;
N-4-hydroxybenzyl-5-(3-chlorophenyl)furan-2-carboxamide ("18"), ESI 328;
N-(benzo-2,1,3-thiadiazol-5-ylmethyl)-5-(3-chlorophenyl)furan-2-carboxamide ("19"), ESI 370;
N-2-methoxybenzyl-5-(3-chlorophenyl)furan-2-carboxamide ("32"), ESI 342.

An analogous procedure to 3.3 starting from "32" gives
N-2-hydroxybenzyl-5-(3-chlorophenyl)furan-2-carboxamide ("33"), ESI 328.

The following compounds are obtained analogously
N-3-fluorobenzyl-5-(4-hydroxyphenyl)furan-2-carboxamide ("78"), ESI 312;
N-2-hydroxybenzyl-5-(4-hydroxyphenyl)furan-2-carboxamide ("77"), ESI 310;

N—[(S)-1-(3-hydroxyphenyl)ethyl]-5-(4-hydroxyphenyl) furan-2-carboxamide ("79"), ESI 310;

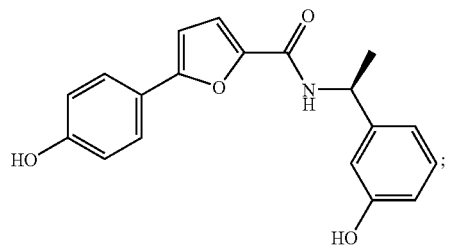

ESI 324

N—[(R)-1-(3-hydroxyphenyl)ethyl]-5-(4-hydroxyphenyl) furan-2-carboxamide ("80"), ESI 324;
N-3-hydroxybenzyl-5-(3-hydroxyphenyl)furan-2-carboxamide ("82"), ESI 310;
N-3-chlorobenzyl-5-(3-hydroxyphenyl)furan-2-carboxamide ("83"), ESI 328;
N-3-benzyloxybenzyl-5-(2-methyl-4-methoxyphenyl)furan-2-carboxamide ("84"), ESI 414;
N-3-methoxybenzyl-5-(2-methyl-4-methoxyphenyl)furan-2-carboxamide ("85"), ESI 338;

EXAMPLE 4

The preparation of N-3-hydroxybenzyl-2-(4-hydroxyphenyl)thioazole-5-carboxamide ("4") is carried out analogously to the following scheme:

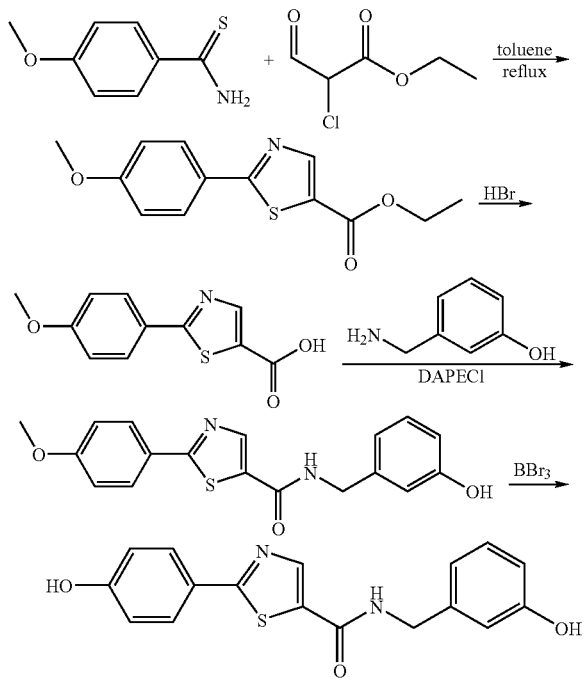

4.1 A solution of 5.00 g (29.9 mmol) of 4-methoxythiobenzamide and 4.50 g (29.9 mmol) of ethyl 2-chloro-3-oxopropionate in 200 ml of toluene is heated at the boil on a water separator for 3 hours. The solution is allowed to cool, and saturated aqueous sodium hydrogencarbonate solution is added. The organic phase is separated off, dried over sodium sulfate and evaporated: ethyl 2-(4-methoxyphenyl)thiazole-5-carboxylate as colourless solid; ESI 264.

4.2 A solution of 3.50 g (13.3 mmol) of ethyl 2-(4-methoxyphenyl)thiazole-5-carboxylate in 20 ml of 48% aqueous hydrobromic acid is heated at 100° C. for 18 hours. The mixture is allowed to cool and extracted with tert-butyl methyl ether. The organic phase is dried over sodium sulfate and evaporated: 2-(4-methoxyphenyl)thiazole-5-carboxylic acid as colourless solid; ESI 236.

4.3 422 mg (2.21 mmol) of N-(3-dimethylaminopropyl)-N'-ethylcarbodiimide hydrochloride (DAPECl) are added to a solution of 400 mg (1.70 mmol) of 2-(4-methoxyphenyl)thiazole-5-carboxylic acid and 209 mg (1.70 mmol) of 3-hydroxybenzylamine in 2 ml of DMF, and the mixture is stirred at room temperature for 18 hours. The reaction mixture is added to water, and the precipitate formed is filtered off: N-3-hydroxybenzyl-2-(4-methoxyphenyl)thiazole-5-carboxamide as colourless solid; ESI 341.

4.4 43 µl of boron tribromide are added to a solution of 50 mg (0.147 mmol) of N-3-hydroxybenzyl-2-(4-methoxyphenyl)thiazole-5-carboxamide in 5 ml of dichloromethane, and the mixture is stirred at room temperature for 18 hours. 3 ml of methanol are slowly added dropwise to the reaction. The reaction mixture is evaporated, methanol is added to the residue, the mixture is stirred for 10 minutes and re-evaporated: N-3-hydroxybenzyl-2-(4-hydroxyphenyl)thiazole-5-carboxamide as colourless solid; ESI 327.

EXAMPLE 5

The preparation of N-3-chlorobenzyl-2-(3-amino-1H-indazol-5-yl)-3H-imidazole-4-carboxamide ("5") is carried out analogously to the following scheme:

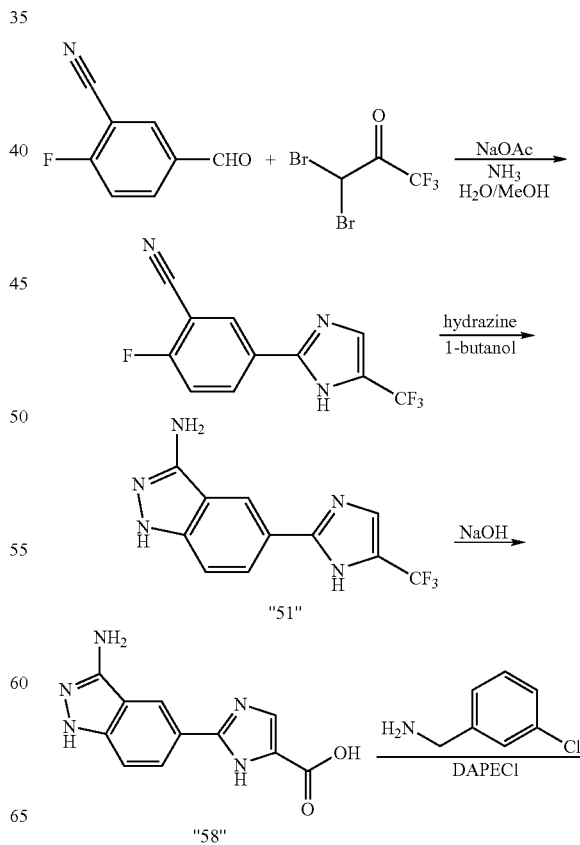

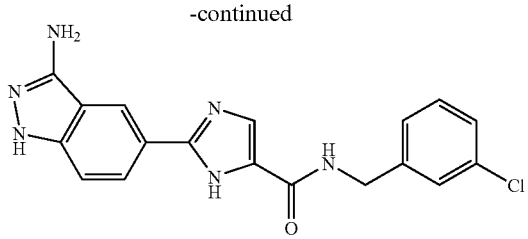

5.1 16.2 g (60.0 mmol) of 1,1-dibromo-3,3,3-trifluoroacetone are mixed with 68 ml of water, and 16.3 g (120 mmol) of sodium acetate trihydrate are added. This solution is heated to 90° C. and added in one portion to a previously prepared suspension of 8.95 g (60.0 mmol) of 2-fluoro-4-formylbenzonitrile in 300 ml of methanol and 84 ml of conc. ammonia. The reaction mixture is stirred at room temperature for 40 hours. It is concentrated to a volume of about 200 ml, and the precipitate formed is filtered off: crude 2-fluoro-5-(5-trifluoromethyl-1H-imidazol-2-yl)benzonitrile as yellow-brown solid (ESI 256), which is employed without further purification for subsequent reactions.

5.2 1.17 ml (24 mmol) of hydrazinium hydroxide are added to a solution of 2.00 g of 2-fluoro-5-(5-trifluoromethyl-1H-imidazol-2-yl)benzonitrile (about 50%, about 3.9 mmol) in 20 ml of 1-butanol, and the mixture is heated at 100° C. for 3 hours. The reaction mixture is evaporated, and the residue is taken up in ethyl acetate. The precipitate formed is filtered off and dried: 5-(5-trifluoromethyl-1H-imidazol-2-yl)-1H-indazol-3-ylamine ("51") as yellow solid; ESI 268.

5.3 A suspension of 733 mg (3.14 mmol) of 5-(5-trifluoromethyl-1H-imidazol-2-yl)-1H-indazol-3-ylamine in 10 ml of 3 normal aqueous NaOH is stirred at room temperature for 3 hours, during which a dark solution forms. This solution is brought to a pH of 3.5 using hydrochloric acid, and the precipitate formed is filtered off: 2-(3-amino-1H-indazol-5-yl)-3H-imidazole-4-carboxylic acid ("58") as yellow-orange solid; ESI 244.

5.4 125 mg (0.65 mmol) of N-(3-dimethylaminopropyl)-N'-ethylcarbodiimide hydrochloride (DAPECI) are added to a solution of 122 mg (0.500 mmol) of 2-(3-amino-1H-indazol-5-yl)-3H-imidazole-4-carboxylic acid and 70.8 mg (0.5 mmol) of 3-chlorobenzylamine in 2 ml of DMF, and the mixture is stirred at room temperature for 18 hours. The reaction mixture is added to saturated sodium hydrogencarbonate solution, and the precipitate formed is filtered off: N-3-chlorobenzyl-2-(3-amino-1H-indazol-5-yl)-3H-imidazole-4-carboxamide ("5") as colourless solid; ESI 367.

The following compounds are obtained analogously
N-3-hydroxybenzyl-2-(3-amino-1H-indazol-5-yl)-3H-imidazole-4-carboxamide ("35"),
N-3-methoxybenzyl-2-(3-amino-1H-indazol-5-yl)-3H-imidazole-4-carboxamide ("36"),
N—[(R)-1-(3-methoxyphenyl)ethyl]-2-(3-amino-1H-indazol-5-yl)-3H-imidazole-4-carboxamide ("37"),
N-3,5-difluorobenzyl-2-(3-amino-1H-indazol-5-yl)-3H-imidazole-4-carboxamide ("38"),
N—[(R)-1-(3-hydroxyphenyl)ethyl]-2-(3-amino-1H-indazol-5-yl)-3H-imidazole-4-carboxamide ("39").

EXAMPLE 6

The preparation of N-3-hydroxybenzyl-2-(3-amino-1H-indazol-6-yl)oxazole-4-carboxamide ("40") is carried out analogously to the following scheme:

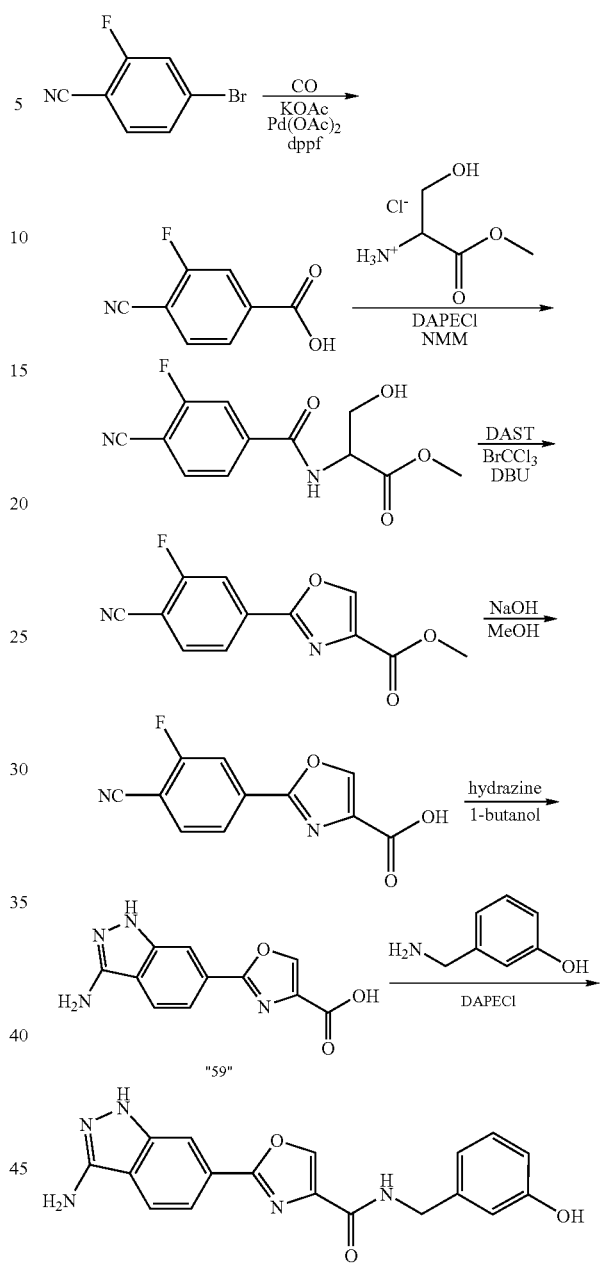

6.1 A solution of 7.00 g (35 mmol) of 4-bromo-3-fluorobenzonitrile is dissolved in a mixture of 44 ml of dimethyl sulfoxide and 9 ml of water. 7.30 g (74.4 mmol) of potassium acetate, 165 mg (0.74 mmol of palladium(II) acetate and 1.03 g (1.86 mmol) of 1,1-bis(diphenylphosphino)ferrocene are added. The suspension formed is treated with carbon monoxide at a pressure of 25 bar in an autoclave for 20 hours with stirring. The reaction mixture is rendered alkaline using 1 N NaOH and extracted with ethyl acetate. The aqueous phase is acidified using conc. hydrochloric acid and extracted with ethyl acetate. The organic phase is dried over sodium sulfate and evaporated, giving 4-cyano-3-fluorobenzoic acid as colourless crystals; ESI 166.

The following steps are carried out analogously to Example 2.1-2.4, giving N-3-hydroxybenzyl-2-(3-amino-1H-indazol-5-yl)oxazole-4-carboxamide ("40").

The following compounds are obtained analogously
N—[(R)-1-(3-methoxyphenyl)ethyl]-2-(3-amino-1H-indazol-5-yl)oxazole-4-carboxamide ("41") and
N-3-chlorobenzyl-2-(3-amino-1H-indazol-5-yl)oxazole-4-carboxamide ("50"),
N-3-chlorobenzyl-2-(3-amino-1H-indazol-6-yl)oxazole-4-carboxamide ("81"), ESI 368;
N-3-hydroxybenzyl-2-(3-amino-1H-indazol-6-yl)oxazole-4-carboxamide ("89"), ESI 350.

EXAMPLE 7

The preparation of N-3-hydroxybenzyl-5-(3-amino-1H-indazol-5-yl)furan-2-carboxamide ("42") is carried out analogously to the following scheme:

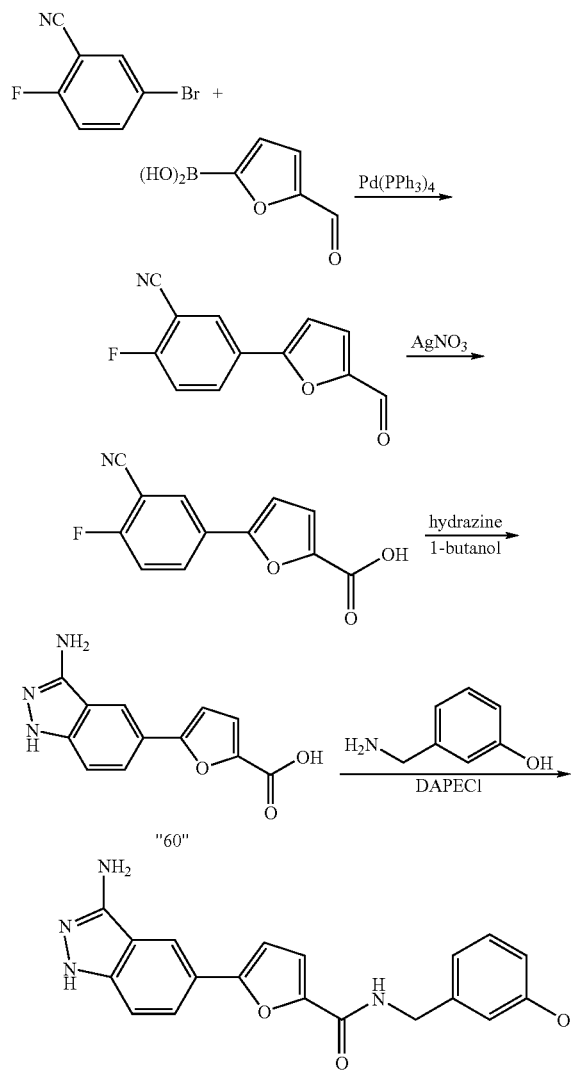

7.1 8.00 g (75.5 mmol) of sodium carbonate and 900 mg (0.80 mmol) of tetrakis(triphenylphosphine)palladium(0) are added to a solution of 5.00 g (25.0 mmol) of 5-bromo-2-fluorobenzonitrile and 3.50 g (25.0 mmol) of 5-formylfuran-2-boronic acid in a mixture of 25 ml of ethylene glycol dimethyl ether and 25 ml of ethanol, and the mixture is heated at the boil for 24 hours. The reaction mixture is partitioned between water and ethyl acetate. The organic phase is dried over sodium sulfate and evaporated, and the residue is chromatographed on a silica-gel column with petroleum ether/ethyl acetate as eluent: 2-fluoro-5-(5-formylfuran-2-yl)benzonitrile as colourless solid; ESI 216.

7.2 A solution of 475 mg (2.80 mmol) of silver nitrate in 5 ml of water is combined with a solution of 224 mg (5.60 mmol) of sodium hydroxide in 5 ml of water. 300 mg (1.39 mmol) of 2-fluoro-5-(5-formylfuran-2-yl)benzonitrile are added in portions to this solution, and the resultant dark reaction mixture is stirred at room temperature for 24 hours. The reaction mixture is filtered, and the filtrate is acidified using concentrated hydrochloric acid.

The precipitate formed is filtered off: 5-(3-cyano-4-fluorophenyl)furan-2-carboxylic acid as colourless solid; ESI 232.

The following reactions are carried out analogously to Example 5.2 and 5.4, giving N-3-hydroxybenzyl-5-(3-amino-1H-indazol-5-yl)furan-2-carboxamide ("42").

An analogous procedure gives
N-3-chlorobenzyl-5-(3-amino-1H-indazol-5-yl)furan-2-carboxamide ("43").

EXAMPLE 8

The preparation of N-3-hydroxybenzyl-5-(3-amino-1H-indazol-5-yl)furan-2-carboxamide ("62") is carried out analogously to the following scheme:

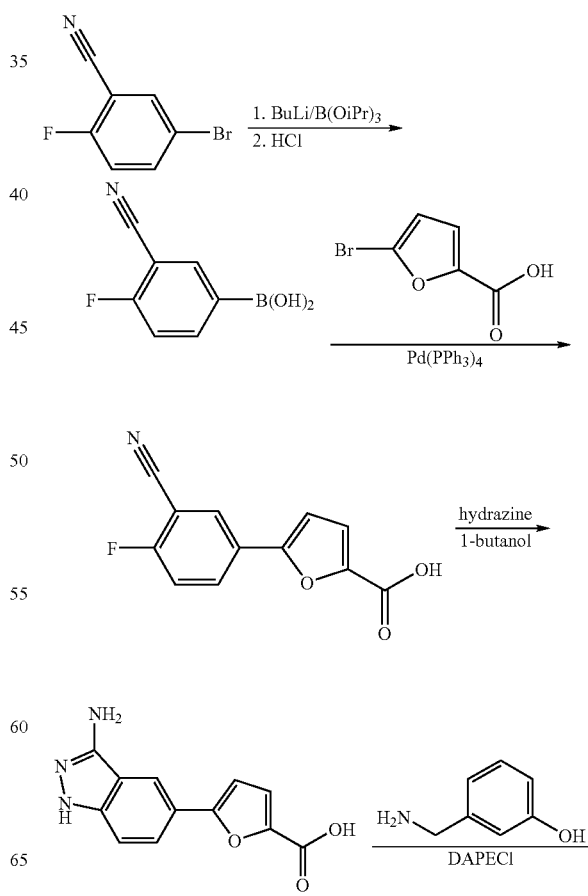

-continued

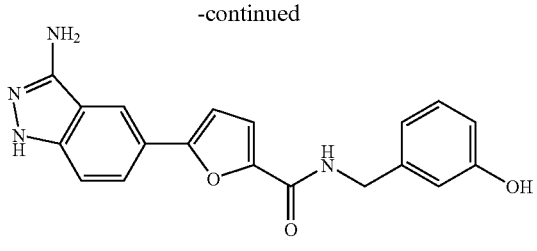

1. A solution of 5.00 g (25.0 mmol) of 5-bromo-2-fluorobenzonitrile and 5.64 g (30.0 mmol) of triisopropyl borate in a mixture of 10 ml of THF and 40 ml of toluene is cooled to −70° C. under nitrogen. At this temperature, 12 ml of a 15% solution of n-butyllithium in hexane (30 mmol) are added dropwise over the course of one hour. The reaction mixture is slowly warmed to −20° C., and 25 ml of 1 N HCl are then added. After warming to room temperature, the organic phase is separated off, dried over sodium sulfate and evaporated. The solid residue is taken up in tert-butyl methyl ether, and the precipitate is filtered and dried: 3-cyano-4-fluorobenzeneboronic acid as colourless solid, ESI 166.

2. 260 mg (0.23 mmol) of tetrakis(triphenylphosphine)palladium(0) are added under nitrogen to a solution of 1.30 g (7.88 mmol) of 3-cyano-4-fluorobenzeneboronic acid and 1.62 g (8.50 mmol) of 5-bromo-2-furanoic acid in a mixture of 10 ml of toluene and 8 ml of THF, and a solution of 1.40 g (16.7 mmol) of sodium hydrogencarbonate in 10 ml of water is added. The reaction mixture is heated at the boil for 3 hours with vigorous stirring. After cooling, the reaction mixture is partitioned between water and ethyl acetate. The aqueous phase is acidified using conc. HCl and extracted with ethyl acetate. The organic phase is dried over sodium sulfate and evaporated: 5-(3-cyano-4-fluorophenyl)furan-2-carboxylic acid as yellowish solid, ESI 232.

3. 1.85 g (37.0 mmol) of hydrazinium hydroxide are added to a solution of 870 mg (3.76 mmol) of 5-(3-cyano-4-fluorophenyl)furan-2-carboxylic acid in 20 ml of 1-butanol, and the mixture is heated at 80° C. for 12 hours. The precipitate formed is filtered off and washed with methanol: 5-(3-amino-1H-indazol-5-yl)furan-2-carboxylic acid as colourless solid, ESI 244.

4. 144 mg (0.75 mmol) of N-(3-dimethylaminopropyl)-N'-ethylcarbodiimide hydrochloride (DAPECl) are added to a solution of 146 mg (0.60 mmol) of 5-(3-amino-1H-indazol-5-yl)furan-2-carboxylic acid and 73.9 mg (0.60 mmol) of 3-hydroxybenzylamine in 1 ml of DMF, and the mixture is stirred at room temperature for 4 hours. Water is added to the reaction mixture, which is extracted with ethyl acetate. The organic phase is dried over sodium sulfate and evaporated, and the residue is purified by preparative HPLC, giving N-3-hydroxybenzyl-5-(3-amino-1H-indazol-5-yl)furan-2-carboxamide ("62") as yellowish solid, ESI 349.

The following compounds are obtained analogously
N-3-hydroxybenzyl-5-(3-amino-1H-indazol-6-yl)furan-2-carboxamide ("61"), ESI 349;
N-3-chlorobenzyl-5-(3-amino-1H-indazol-5-yl)thiophene-2-carboxamide ("63"), ESI 383;
N-3-methoxybenzyl-5-(3-amino-1H-indazol-5-yl)furan-2-carboxamide ("64"), ESI 363;
N-3-chlorobenzyl-5-(3-amino-1H-indazol-5-yl)furan-2-carboxamide ("65"), ESI 367;
N-3-hydroxybenzyl-5-(3-amino-1H-indazol-5-yl)thiophene-2-carboxamide ("66"), ESI 365;
N-3-methoxybenzyl-5-(3-amino-1H-indazol-5-yl)thiophene-2-carboxamide ("67"), ESI 379;
N—[(R)-1-(3-methoxyphenyl)ethyl]-5-(3-amino-1H-indazol-5-yl)thiophene-2-carboxamide ("68"),

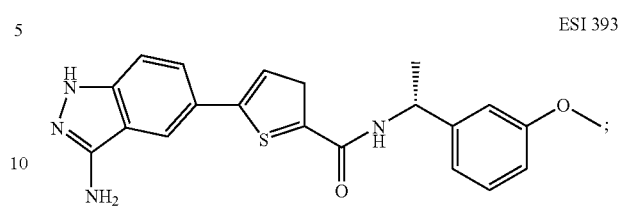

N-3-methoxybenzyl-5-(3-amino-1H-indazol-6-yl)furan-2-carboxamide ("69"), ESI 363;
N—[(R)-1-(3-methoxyphenyl)ethyl]-5-(3-amino-1H-indazol-5-yl)furan-2-carboxamide ("70"), ESI 377;
N—[(S)-1-(3-methoxyphenyl)ethyl]-5-(3-amino-1H-indazol-5-yl)furan-2-carboxamide ("71"), ESI 377;
N-3-trifluoromethoxybenzyl-5-(3-amino-1H-indazol-5-yl)furan-2-carboxamide ("72"), ESI 417;
N-[1-(3-methoxyphenyl)pentyl]-5-(3-amino-1H-indazol-5-yl)furan-2-carboxamide ("73"), ESI 419;
N-(3-trifluoromethoxyphenyl)-5-(3-amino-1H-indazol-5-yl)furan-2-carboxamide ("74"), ESI 403

EXAMPLE 9

The preparation of N-p-tolyl-3-amino-5-[5-(3-hydroxybenzylcarbamoyl)-furan-2-yl]indazole-1-carboxamide ("75") is carried out analogously to the following scheme:

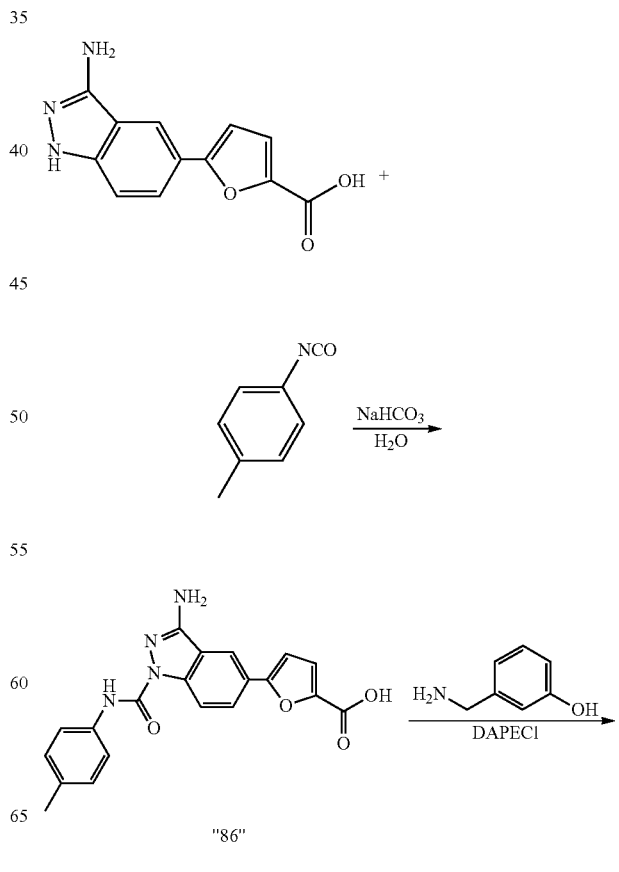

-continued

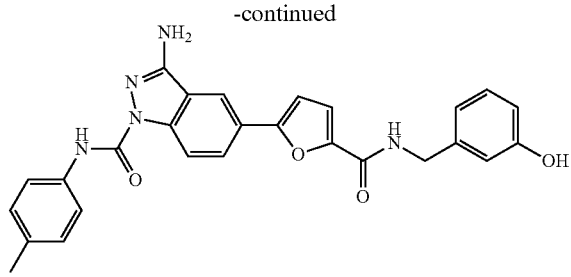

A solution of 140 mg (0.576 mmol) of 5-(3-amino-1H-indazol-5-yl)furan-2-carboxylic acid and 128 mg (1.52 mmol) of sodium hydrogencarbonate in 5 ml of water is heated to 80° C., and 202 mg (1.52 mmol) of p-tolyl isocyanate are added. The mixture is stirred vigorously at this temperature for 1 hour. The mixture is allowed to cool, and the precipitate formed is filtered off. The filtrate is brought to a pH of 2 using 1 N HCl and extracted with ethyl acetate. The organic phase is dried over sodium sulfate and evaporated: 5-(3-amino-1-p-tolylcarbamoyl-1H-indazol-5-yl)furan-2-carboxylic acid ("86") as colourless solid, ESI 377.

Analogously to Example 8.4, reaction thereof with 3-hydroxybenzylamine gives the compound N-p-tolyl-3-amino-5-[5-(3-hydroxybenzylcarbamoyl)furan-2-yl]indazole-1-carboxamide ("75"), ESI 482.

EXAMPLE 10

The preparation of N-3-hydroxybenzyl-5-(3-amino-1-methyl-1H-indazol-5-yl)furan-2-carboxamide ("76") is carried out analogously to the following scheme:

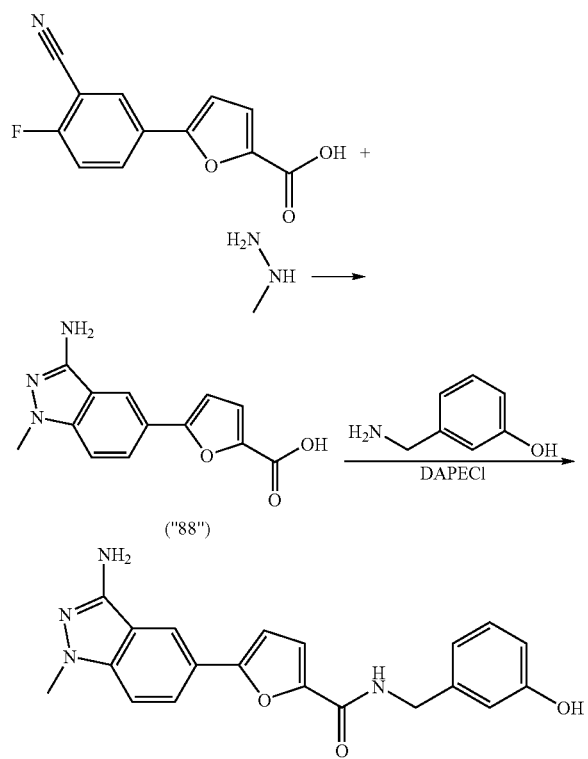

A solution of 340 mg (1.47 mmol) of 5-(3-cyano-4-fluorophenyl)furan-2-carboxylic acid and 266 mg (5.65 mmol) of methylhydrazine in 5 ml of 1-butanol is heated at 10° C. for 18 hours. After cooling to room temperature, the reaction mixture is evaporated, the residue is taken up in 1 N HCl, and the precipitate formed is filtered off: 5-(3-amino-1-methyl-1H-indazol-5-yl)furan-2-carboxylic acid ("88") as colourless solid, ESI 257.

Analogously to Example 8.4, reaction thereof with 3-hydroxybenzylamine gives the compound N-3-hydroxybenzyl-5-(3-amino-1-methyl-1H-indazol-5-yl)furan-2-carboxamide ("76"), ESI 363.

The following examples relate to pharmaceutical preparations:

EXAMPLE A

Injection Vials

A solution of 100 g of an active ingredient according to the invention and 5 g of disodium hydrogenphosphate in 3 l of bidistilled water is adjusted to pH 6.5 using 2N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient according to the invention with 100 g of soya lecithin and 1400 g of cocoa butter is melted, poured into moulds and allowed to cool. Each suppository contains 20 mg of active ingredient.

EXAMPLE C

Solution

A solution is prepared from 1 g of an active ingredient according to the invention, 9.38 g of $NaH_2PO_4.2H_2O$, 28.48 g of $Na_2HPO_4.2H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient according to the invention are mixed with 99.5 g of Vaseline under aseptic conditions.

EXAMPLE E

Tablets

A mixture of 1 kg of active ingredient according to the invention, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

EXAMPLE F

Dragees

Tablets are pressed analogously to Example E and subsequently coated in a conventional manner with a coating of sucrose, potato starch, talc, tragacanth and dye.

EXAMPLE G

Capsules 2 kg of active ingredient according to the invention are introduced into hard gelatine capsules in a conventional manner in such a way that each capsule contains 20 mg of the active ingredient.

EXAMPLE H

Ampoules

A solution of 1 kg of an active ingredient according to the invention in 60 l of bidistilled water is sterile filtered, transferred into ampoules, lyophilised under sterile conditions and sealed under sterile conditions. Each ampoule contains 10 mg of active ingredient.

The invention claimed is:
1. A compound selected from:
N-3-hydroxybenzyl-2-(4-hydroxyphenyl)-3H-imidazole-4-carboxamide,
N-3-chlorobenzyl-2-(3-amino-1H-indazol-5-yl)-3H-imidazole-4-carboxamide,
N-3-hydroxybenzyl-2-(2,4-dihydroxyphenyl)-3H-imidazole-4-carboxamide,
N-4-hydroxyphenyl-2-(4-hydroxyphenyl)-3H-imidazole-4-carboxamide,
N-3-hydroxyphenyl-2-(3-hydroxyphenyl)-3H-imidazole-4-carboxamide,
N-4-hydroxyphenyl-2-(3-hydroxyphenyl)-3H-imidazole-4-carboxamide,
N-3-hydroxyphenyl-2-(4-hydroxyphenyl)-3H-imidazole-4-carboxamide,
N-3-hydroxybenzyl-2-(4-hydroxy-2-methylphenyl)-3H-imidazole-4-carboxamide,
N-3-fluorobenzyl-2-(4-hydroxyphenyl)-3H-imidazole-4-carboxamide,
N-4-hydroxybenzyl-2-(4-hydroxyphenyl)-3H-imidazole-4-carboxamide,
N-4-hydroxybenzyl-2-(3-hydroxyphenyl)-3H-imidazole-4-carboxamide,
N-3-hydroxybenzyl-2-(3-hydroxyphenyl)-3H-imidazole-4-carboxamide,
N-3-fluorobenzyl-2-(3-hydroxyphenyl)-3H-imidazole-4-carboxamide,
N-3-fluorobenzyl-2-(4-fluorophenyl)-3H-imidazole-4-carboxamide,
N-3-hydroxybenzyl-2-(4-fluorophenyl)-3H-imidazole-4-carboxamide,
N-2-methoxybenzyl-2-(4-hydroxyphenyl)-3H-imidazole-4-carboxamide,
N-3-hydroxybenzyl-2-(3-amino-1H-indazol-5-yl)-3H-imidazole-4-carboxamide,
N-3-methoxybenzyl-2-(3-amino-1H-indazol-5-yl)-3H-imidazole-4-carboxamide,
N—[(R)-1-(3-methoxyphenyl)ethyl]-2-(3-amino-1H-indazol-5-yl)-3H-imidazole-4-carboxamide,
N-3,5-difluorobenzyl-2-(3-amino-1H-indazol-5-yl)-3H-imidazole-4-carboxamide,
N—[(R)-1-(3-hydroxyphenyl)ethyl]-2-(3-amino-1H-indazol-5-yl)-3H-imidazole-4-carboxamide,
N-3-hydroxybenzyl-2-(3-bromophenyl)-3H-imidazole-4-carboxamide,
N-3-methoxybenzyl-2-(3-bromophenyl)-3H-imidazole-4-carboxamide,
N-3-chlorobenzyl-2-(3-bromophenyl)-3H-imidazole-4-carboxamide,
N-3-hydroxybenzyl-2-(3-chlorophenyl)-3H-imidazole-4-carboxamide,
N-3-methoxybenzyl-2-(3-chlorophenyl)-3H-imidazole-4-carboxamide, and
N-3-chlorobenzyl-2-(3-chlorophenyl)-3H-imidazole-4-carboxamide,
or pharmaceutically usable salts and stereoisomers thereof.
2. A compound selected from:
N-3-hydroxybenzyl-2-(3-hydroxyphenyl)oxazole-4-carboxamide,
N-3-hydroxybenzyl-2-(4-hydroxyphenyl)oxazole-4-carboxamide,
N—[(R)-1-(3-hydroxyphenyl)ethyl]-2-(3-hydroxyphenyl)oxazole-4-carboxamide,
N-3-hydroxyphenyl-2-(3-hydroxyphenyl)oxazole-4-carboxamide,
N-4-hydroxybenzyl-2-(3-hydroxyphenyl)oxazole-4-carboxamide,
N-4-hydroxyphenyl-2-(3-hydroxyphenyl)oxazole-4-carboxamide,
N-3-fluorobenzyl-2-(4-hydroxyphenyl)oxazole-4-carboxamide,
N-3-fluorobenzyl-2-(3-chloro-6-methoxyphenyl)oxazole-4-carboxamide,
N-3-hydroxybenzyl-2-(3-amino-1H-indazol-5-yl)oxazole-4-carboxamide,
N—[(R)-1-(3-methoxyphenyl)ethyl]-2-(3-amino-1H-indazol-5-yl)oxazole-4-carboxamide,
N-3,5-difluorobenzyl-2-(3-hydroxyphenyl)oxazole-4-carboxamide,
N-2-methoxybenzyl-2-(4-hydroxyphenyl)oxazole-4-carboxamide,
N-3-hydroxybenzyl-2-(3-chloro-6-methoxyphenyl)oxazole-4-carboxamide,
N—[(S)-1-(3-hydroxyphenyl)ethyl]-2-(3-chloro-6-methoxyphenyl)oxazole-4-carboxamide,
N—[(R)-1-(3-hydroxyphenyl)ethyl]-2-(3-chloro-6-methoxyphenyl)oxazole-4-carboxamide,
N-3-methoxybenzyl-2-(3-chloro-6-methoxyphenyl)oxazole-4-carboxamide,
N-3-chlorobenzyl-2-(3-amino-1H-indazol-5-yl)oxazole-4-carboxamide, and
N-3-chlorobenzyl-2-(3-amino-1H-indazol-6-yl)oxazole-4-carboxamide,
or pharmaceutically usable salts and stereoisomers thereof.
3. A compound selected from:
N-3-hydroxybenzyl-5-(4-hydroxyphenyl)furan-2-carboxamide,
N-3-hydroxybenzyl-5-(3-chlorophenyl)furan-2-carboxamide,
N-4-hydroxybenzyl-5-(3-chlorophenyl)furan-2-carboxamide,
N-2-methoxybenzyl-5-(3-chlorophenyl)furan-2-carboxamide,
N-2-hydroxybenzyl-5-(3-chlorophenyl)furan-2-carboxamide,

N-3-hydroxybenzyl-5-(3-amino-1H-indazol-5-yl)furan-2-carboxamide,
N-3-hydroxybenzyl-5-(3-amino-1H-indazol-6-yl)furan-2-carboxamide,
N-3-hydroxybenzyl-5-(3-amino-1H-indazol-5-yl)furan-2-carboxamide,
N-3-methoxybenzyl-5-(3-amino-1H-indazol-5-yl)furan-2-carboxamide,
N-3-chlorobenzyl-5-(3-amino-1H-indazol-5-yl)furan-2-carboxamide,
N-3-methoxybenzyl-5-(3-amino-1H-indazol-6-yl)furan-2-carboxamide,
N—[(R)-1-(3-methoxyphenyl)ethyl]-5-(3-amino-1H-indazol-5-yl)furan-2-carboxamide,
N—[(S)-1-(3-methoxyphenyl)ethyl]-5-(3-amino-1H-indazol-5-yl)furan-2-carboxamide;
N-3-trifluoromethoxybenzyl-5-(3-amino-1H-indazol-5-yl)furan-2-carboxamide,
N-[1-(3-methoxyphenyl)pentyl]-5-(3-amino-1H-indazol-5-yl)furan-2-carboxamide,
N-(3-trifluoromethoxyphenyl)-5-(3-amino-1H-indazol-5-yl)furan-2-carboxamide,
N-p-tolyl-3-amino-5-[5-(3-hydroxybenzylcarbamoyl)furan-2-yl]indazole-1-carboxamide,
N-3-hydroxybenzyl-5-(3-amino-1-methyl-1H-indazol-5-yl)furan-2-carboxamide,
N-2-hydroxybenzyl-5-(4-hydroxyphenyl)furan-2-carboxamide,
N-3-fluorobenzyl-5-(4-hydroxyphenyl)furan-2-carboxamide,
N—[(S)-1-(3-hydroxyphenyl)ethyl]-5-(4-hydroxyphenyl)furan-2-carboxamide,
N—[(R)-1-(3-hydroxyphenyl)ethyl]-5-(4-hydroxyphenyl)furan-2-carboxamide,
N-3-hydroxybenzyl-5-(3-hydroxyphenyl)furan-2-carboxamide,
N-3-chlorobenzyl-5-(3-hydroxyphenyl)furan-2-carboxamide,
N-p-tolyl-3-amino-5-[5-(3-hydroxybenzylcarbamoyl)furan-2-yl]indazole-1-carboxamide,
N-3-benzyloxybenzyl-5-(2-methyl-4-methoxyphenyl)furan-2-carboxamide, and
N-3-methoxybenzyl-5-(2-methyl-4-methoxyphenyl)furan-2-carboxamide,
or pharmaceutically usable salts and stereoisomers thereof.

4. A compound selected from:
N-3-chlorobenzyl-5-(3-amino-1H-indazol-5-yl)thiophene-2-carboxamide,
N-3-hydroxybenzyl-5-(3-amino-1H-indazol-5-yl)thiophene-2-carboxamide,
N-3-methoxybenzyl-5-(3-amino-1H-indazol-5-yl)thiophene-2-carboxamide, and
N—[(R)-1-(3-methoxyphenyl)ethyl]-5-(3-amino-1H-indazol-5-yl)thiophene-2-carboxamide,
or pharmaceutically usable salts and stereoisomers thereof.

5. A stereoisomeric mixture comprising a compound according to claim 1 and a stereoisomer thereof.

6. A compound according to claim 1, wherein said compound is N-3-hydroxybenzyl-2-(4-hydroxyphenyl)-3H-imidazole-4-carboxamide or a pharmaceutically acceptable salt thereof.

7. A pharmaceutical composition comprising at least one compound according to claim 1, and at least one excipient and/or adjuvant.

8. A pharmaceutical composition comprising at least one compound according to claim 1, and at least one further medicament active ingredient.

9. A method for the treatment of a disease selected from diabetes mellitus, diabetic nephropathy, diabetic neuropathy, diabetic angiopathy, microangiopathy, cardiac fibroses after myocardial infarction, cardiac hypertrophy, cardiac insufficiency, arteriosclerosis, glomerulosclerosis, nephrosclerosis, nephritis, nephropathy, electrolyte excretion disorder, liver cirrhosis, lung fibrosis, fibrosing pancreatitis, rheumatism and arthritis, Crohn's disease, chronic bronchitis, radiation fibrosis, sclerormatitis, cystic fibrosis, scarring, and Alzheimer's disease, comprising administering to a patient in need thereof an effective amount of a compound according to claim 1.

10. A method according to claim 9, where said patient is suffering from is diabetes mellitus, diabetic nephropathy, diabetic neuropathy, diabetic angiopathy or microangiopathy.

11. A method according to claim 9, where said patient is suffering from cardiac fibroses after myocardial infarction, cardiac hypertrophy, cardiac insufficiency or arteriosclerosis.

12. A method according to claim 9, where said patient is suffering from renal disease, and said renal disease is glomerulosclerosis, nephrosclerosis, nephritis, nephropathy or electrolyte excretion disorder.

13. A method according to claim 9, where said patient is suffering from liver cirrhosis, lung fibrosis, fibrosing pancreatitis, rheumatism and arthritis, Crohn's disease, chronic bronchitis, radiation fibrosis, sclerormatitis, cystic fibrosis, scarring, or Alzheimer's disease.

14. A method for treating diabetes, comprising administering to a patient in need thereof an effective amount of a compound according to claim 1.

15. A method for treating a patient suffering from for anti-infectious therapy, for increasing learning ability and attention, for the treating cell ageing and/or stress, and for treating of tinnitus, comprising administering to said patient an effective amount of a compound according to claim 1.

16. A kit comprising separate packs of (a) an effective amount of a compound according to claim 1, and
(b) an effective amount of a further medicament active ingredient.

17. A pharmaceutical composition comprising at least one compound according to claim 2, and at least one excipient and/or adjuvant.

18. A pharmaceutical composition comprising at least one compound according to claim 2, and at least one further medicament active ingredient.

19. A method for the treatment of a disease selected from diabetes mellitus, diabetic nephropathy, diabetic neuropathy, diabetic angiopathy, microangiopathy, cardiac fibroses after myocardial infarction, cardiac hypertrophy, cardiac insufficiency, arteriosclerosis, glomerulosclerosis, nephrosclerosis, nephritis, nephropathy, electrolyte excretion disorder, liver cirrhosis, lung fibrosis, fibrosing pancreatitis, rheumatism and arthritis, Crohn's disease, chronic bronchitis, radiation fibrosis, sclerormatitis, cystic fibrosis, scarring, and Alzheimer's disease, comprising administering to a patient in need thereof an effective amount of a compound according to claim 2.

20. A method according to 19, where said patient is suffering from is diabetes mellitus, diabetic nephropathy, diabetic neuropathy, diabetic angiopathy or microangiopathy.

21. A method according to 19, where said patient is suffering from cardiac fibroses after myocardial infarction, cardiac hypertrophy, cardiac insufficiency or arteriosclerosis.

22. A method according to 19, where said patient is suffering from glomerulosclerosis, nephrosclerosis, nephritis, nephropathy or electrolyte excretion disorder.

23. A method according to 19, where said patient is suffering from liver cirrhosis, lung fibrosis, fibrosing pancreatitis, rheumatism and arthritis, Crohn's disease, chronic bronchitis, radiation fibrosis, sclerormatitis, cystic fibrosis, scarring, or Alzheimer's disease.

24. A method for treating diabetes, comprising administering to a patient in need thereof an effective amount of a compound according to claim 2.

25. A method for treating a patient suffering from for anti-infectious therapy, for increasing learning ability and attention, for the treating cell ageing and/or stress, and for treating of tinnitus, comprising administering to said patient an effective amount of a compound according to claim 2.

26. A kit comprising separate packs of
   (a) an affective amount of a compound according to claim 2, and
   (b) an effective amount of a further medicament active ingredient.

27. A pharmaceutical composition comprising at least one compound according to claim 3, and at least one excipient and/or adjuvant.

28. A pharmaceutical composition comprising at least one compound according to claim 3, and at least one further medicament active ingredient.

29. A method for the treatment of a disease selected from diabetes mellitus, diabetic nephropathy, diabetic neuropathy, diabetic angiopathy, microangiopathy, cardiac fibroses after myocardial infarction, cardiac hypertrophy, cardiac insufficiency, arteriosclerosis, glomerulosclerosis, nephrosclerosis, nephritis, nephropathy, electrolyte excretion disorder, liver cirrhosis, lung fibrosis, fibrosing pancreatitis, rheumatism and arthritis, Crohn's disease, chronic bronchitis, radiation fibrosis, sclerormatitis, cystic fibrosis, scarring, and Alzheimer's disease, comprising administering to a patient in need thereof an effective amount of a compound according to claim 3.

30. A method according to claim 29, where said patient is suffering from is diabetes mellitus, diabetic nephropathy, diabetic neuropathy, diabetic angiopathy or microangiopathy.

31. A method according to claim 29, where said patient is suffering from cardiac fibroses after myocardial infarction, cardiac hypertrophy, cardiac insufficiency or arteriosclerosis.

32. A method according to claim 29, where said patient is suffering from glomerulosclerosis, nephrosclerosis, nephritis, nephropathy or electrolyte excretion disorder.

33. A method according to claim 29, where said patient is suffering from liver cirrhosis, lung fibrosis, fibrosing pancreatitis, rheumatism and arthritis, Crohn's disease, chronic bronchitis, radiation fibrosis, sclerormatitis, cystic fibrosis, scarring, or Alzheimer's disease.

34. A method for treating diabetes, comprising administering to a patient in need thereof an effective amount of a compound according to claim 3.

35. A method for treating a patient suffering from for anti-infectious therapy, for increasing learning ability and attention, for the treating cell ageing and/or stress, and for treating of tinnitus, comprising administering to said patient an effective amount of a compound according to claim 3.

36. A kit comprising separate packs of
   (a) an effective amount of a compound according to claim 3, and
   (b) an effective amount of a further medicament active ingredient.

37. A pharmaceutical composition comprising at least one compound according to claim 4, and at least one excipient and/or adjuvant.

38. A pharmaceutical composition comprising at least one compound according to claim 4, and at least one further medicament active ingredient.

39. A method for the treatment of a disease selected from diabetes mellitus, diabetic nephropathy, diabetic neuropathy, diabetic angiopathy, microangiopathy, cardiac fibroses after myocardial infarction, cardiac hypertrophy, cardiac insufficiency, arteriosclerosis, glomerulosclerosis, nephrosclerosis, nephritis, nephropathy, electrolyte excretion disorder, liver cirrhosis, lung fibrosis, fibrosing pancreatitis, rheumatism and arthritis, Crohn's disease, chronic bronchitis, radiation fibrosis, sclerormatitis, cystic fibrosis, scarring, and Alzheimer's disease, comprising administering to a patient in need thereof an effective amount of a compound according to claim 4.

40. A method according to claim 39, where said patient is suffering from diabetes mellitus, diabetic nephropathy, diabetic neuropathy, diabetic angiopathy or microangiopathy.

41. A method according to claim 39, where said patient is suffering from cardiac fibroses after myocardial infarction, cardiac hypertrophy, cardiac insufficiency or arteriosclerosis.

42. A method according to claim 39, where said patient is suffering from glomerulosclerosis, nephrosclerosis, nephritis, nephropathy or electrolyte excretion disorder.

43. A method according to claim 39, where said patient is suffering from liver cirrhosis, lung fibrosis, fibrosing pancreatitis, rheumatism and arthritis, Crohn's disease, chronic bronchitis, radiation fibrosis, sclerormatitis, cystic fibrosis, scarring, or Alzheimer's disease.

44. A method for treating diabetes, comprising administering to a patient in need thereof an effective amount of a compound according to claim 4.

45. A method for treating a patient suffering from for anti-infectious therapy, for increasing learning ability and attention, for the treating cell ageing and/or stress, and for treating of tinnitus, comprising administering to said patient an effective amount of a compound according to claim 4.

46. A kit comprising separate packs of
   (a) an effective amount of a compound according to claim 4, and
   (b) an effective amount of a further medicament active ingredient.

* * * * *

UNITED STATES PATENT AND TRADEMARK OFFICE
CERTIFICATE OF CORRECTION

| | | |
|---|---|---|
| PATENT NO. | : 8,815,924 B2 | |
| APPLICATION NO. | : 11/665854 | |
| DATED | : August 26, 2014 | |
| INVENTOR(S) | : Dieter Dorsch et al. | |

It is certified that error appears in the above-identified patent and that said Letters Patent is hereby corrected as shown below:

On the Title Page:

Item (30)     Foreign Application Priority Data reads:

"October 21, 2008  (DE) .......................... 10 2004 051 277" should read:

--October 21, 2004  (DE) .......................... 10 2004 051 277--

In the Claims

Column 40, Line 14 reads: "suffering from is diabetes mellitus, diabetic nephropathy, dia-" should read: --suffering from diabetes mellitus, diabetic nephropathy, dia- --

Column 40, Line 21 reads: "suffering from renal disease, and said renal disease is glom-" should read: --suffering from glom- --

Column 40, Line 60 reads: "ing from is diabetes mellitus, diabetic nephropathy, diabetic" should read: --ing from diabetes mellitus, diabetic nephropathy, diabetic--

Column 41, Line 38 reads: "suffering from is diabetes mellitus, diabetic nephropathy, dia-" should read: --suffering from diabetes mellitus, diabetic nephropathy, dia- --

Signed and Sealed this
Seventeenth Day of March, 2015

Michelle K. Lee
*Director of the United States Patent and Trademark Office*